US007989062B2

(12) United States Patent
Chakravarty et al.

(10) Patent No.: US 7,989,062 B2
(45) Date of Patent: *Aug. 2, 2011

(54) BIODEGRADABLE CONTINUOUS FILAMENT WEB

(75) Inventors: Jayant Chakravarty, Woodbury, MN (US); Vasily Topolkaraev, Appleton, WI (US); John Herbert Conrad, Alpharetta, GA (US); Stephen Avedis Baratian, Roswell, GA (US); Jared L. Martin, Cumming, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 351 days.

This patent is subject to a terminal disclaimer.

(21) Appl. No.: 12/091,834

(22) PCT Filed: Apr. 7, 2006

(86) PCT No.: PCT/US2006/012948
§ 371 (c)(1),
(2), (4) Date: Apr. 28, 2008

(87) PCT Pub. No.: WO2007/070075
PCT Pub. Date: Jun. 21, 2007

(65) Prior Publication Data
US 2008/0287024 A1    Nov. 20, 2008

Related U.S. Application Data

(63) Continuation-in-part of application No. PCT/US2005/046178, filed on Dec. 15, 2005.

(51) Int. Cl.
*D02G 3/00*    (2006.01)
*D04H 1/00*    (2006.01)
*D04H 13/00*    (2006.01)

(52) U.S. Cl. ......... 428/373; 442/361; 442/362; 442/364
(58) Field of Classification Search .................. 442/361, 442/362, 364; 428/373
See application file for complete search history.

(56) References Cited

U.S. PATENT DOCUMENTS 5,039,783 A    8/1991    Brunelle et al.
(Continued)

FOREIGN PATENT DOCUMENTS

EP    0731198 A2    9/1996
(Continued)

OTHER PUBLICATIONS

Abstract of Korean Patent No. KR1020010057068A, Jul. 4, 2001.
(Continued)

*Primary Examiner* — Norca L Torres-Velazquez
(74) *Attorney, Agent, or Firm* — Dority & Manning, P.A.

(57) ABSTRACT

A biodegradable nonwoven web comprising substantially continuous multicomponent filaments is provided. The filaments comprise a first component and a second component. The first component contains at least one high-melting point aliphatic polyester having a melting point of from about 160° C. to about 250° C. and the second component contains at least one low-melting point aliphatic polyester. The melting point of the low-melting point aliphatic polyester is at least about 30° C. less than the melting point of the high-melting point aliphatic polyester. The low-melting point aliphatic polyester has a number average molecular weight of from about 30,000 to about 120,000 Daltons, a glass transition temperature of less than about 25° C., and an apparent viscosity of from about 50 to about 215 Pascal-seconds, as determined at a temperature of 160° C. and a shear rate of 1000 sec$^{-1}$.

33 Claims, 7 Drawing Sheets

U.S. PATENT DOCUMENTS

| | | |
|---|---|---|
| 5,053,482 A | 10/1991 | Tietz |
| 5,108,820 A | 4/1992 | Kaneko et al. |
| 5,108,827 A | 4/1992 | Gessner |
| 5,188,885 A | 2/1993 | Timmons et al. |
| 5,231,161 A | 7/1993 | Brunelle et al. |
| 5,262,460 A | 11/1993 | Suzuki et al. |
| 5,270,401 A | 12/1993 | Sham et al. |
| 5,292,783 A | 3/1994 | Buchanan et al. |
| 5,336,552 A | 8/1994 | Strack et al. |
| 5,350,624 A | 9/1994 | Georger et al. |
| 5,382,400 A | 1/1995 | Pike et al. |
| 5,407,984 A | 4/1995 | Brunelle et al. |
| 5,432,000 A | 7/1995 | Young, Sr. et al. |
| 5,446,079 A | 8/1995 | Buchanan et al. |
| 5,464,688 A | 11/1995 | Timmons et al. |
| 5,466,517 A | 11/1995 | Eschwey et al. |
| 5,527,976 A | 6/1996 | Takekoshi et al. |
| 5,554,657 A | 9/1996 | Brownscombe et al. |
| 5,559,171 A | 9/1996 | Buchanan et al. |
| 5,580,911 A | 12/1996 | Buchanan et al. |
| 5,593,778 A | 1/1997 | Kondo et al. |
| 5,599,858 A | 2/1997 | Buchanan et al. |
| 5,614,298 A | 3/1997 | Tanaka et al. |
| 5,668,186 A | 9/1997 | Brunelle et al. |
| 5,688,582 A | 11/1997 | Nagaoka et al. |
| 5,753,736 A | 5/1998 | Bhat et al. |
| 5,783,505 A | 7/1998 | Duckett et al. |
| 5,817,199 A | 10/1998 | Brennecke et al. |
| 5,817,721 A | 10/1998 | Warzelhan et al. |
| 5,851,937 A | 12/1998 | Wu et al. |
| 5,895,710 A | 4/1999 | Sasse et al. |
| 5,900,322 A | 5/1999 | Buchanan et al. |
| 5,910,545 A | 6/1999 | Tsai et al. |
| 5,945,480 A | 8/1999 | Wang et al. |
| 5,952,433 A | 9/1999 | Wang et al. |
| 6,045,908 A | 4/2000 | Nakajima et al. |
| 6,063,895 A | 5/2000 | Chung et al. |
| 6,075,118 A | 6/2000 | Wang et al. |
| 6,090,494 A | 7/2000 | Rao |
| 6,177,193 B1 | 1/2001 | Tsai et al. |
| 6,194,483 B1 | 2/2001 | Tsai et al. |
| 6,197,860 B1 | 3/2001 | Tsai et al. |
| 6,201,068 B1 | 3/2001 | Tsai et al. |
| 6,218,321 B1 | 4/2001 | Lorcks et al. |
| 6,225,388 B1 | 5/2001 | Tsai et al. |
| 6,235,393 B1 | 5/2001 | Kimura et al. |
| 6,245,831 B1 | 6/2001 | Tsai et al. |
| 6,258,924 B1 | 7/2001 | Warzelhan et al. |
| 6,268,434 B1 | 7/2001 | Tsai et al. |
| 6,399,716 B2 | 6/2002 | Chung et al. |
| 6,420,027 B2 | 7/2002 | Kimura et al. |
| 6,420,048 B1 | 7/2002 | Wang |
| 6,495,656 B1 | 12/2002 | Haile et al. |
| 6,500,897 B2 | 12/2002 | Wang et al. |
| 6,506,873 B1 | 1/2003 | Ryan et al. |
| 6,525,164 B2 | 2/2003 | Faler |
| 6,544,455 B1 | 4/2003 | Tsai |
| 6,552,124 B2 | 4/2003 | Wang et al. |
| 6,552,162 B1 | 4/2003 | Wang et al. |
| 6,562,938 B2 | 5/2003 | Haile et al. |
| 6,576,576 B1 | 6/2003 | Wang et al. |
| 6,579,934 B1 | 6/2003 | Wang et al. |
| 6,607,996 B1 | 8/2003 | Matsunaga et al. |
| 6,623,853 B2 | 9/2003 | Branum et al. |
| 6,623,854 B2 | 9/2003 | Bond |
| 6,635,799 B1 | 10/2003 | Osborn, III et al. |
| 6,660,211 B2 | 12/2003 | Topolkaraev et al. |
| 6,686,303 B1 | 2/2004 | Haynes et al. |
| 6,709,526 B1 | 3/2004 | Bailey et al. |
| 6,713,595 B2 | 3/2004 | Chung et al. |
| 6,740,401 B1 | 5/2004 | Yahata et al. |
| 6,743,506 B2 | 6/2004 | Bond et al. |
| 6,756,412 B2 | 6/2004 | Muzzy |
| 6,783,854 B2 | 8/2004 | Bond |
| 6,787,493 B1 | 9/2004 | Nagaoka et al. |
| 6,802,895 B2 | 10/2004 | Mackey et al. |
| 6,811,740 B2 | 11/2004 | James et al. |
| 6,838,403 B2 | 1/2005 | Tsai et al. |
| 6,863,971 B2 | 3/2005 | Halahmi et al. |
| 6,872,674 B2 | 3/2005 | Williams et al. |
| 6,890,872 B2 | 5/2005 | Bond et al. |
| 6,890,989 B2 | 5/2005 | Wang et al. |
| 6,905,759 B2 | 6/2005 | Topolkaraev et al. |
| 6,946,195 B2 | 9/2005 | Griffith et al. |
| 6,946,506 B2 | 9/2005 | Bond et al. |
| 6,953,622 B2 | 10/2005 | Tsai et al. |
| 7,001,562 B2 | 2/2006 | Schiffer et al. |
| 7,029,620 B2 | 4/2006 | Gordon et al. |
| 7,037,983 B2 | 5/2006 | Huang et al. |
| 7,053,151 B2 | 5/2006 | Wang et al. |
| 7,060,867 B2 | 6/2006 | Jameson |
| 7,077,994 B2 | 7/2006 | Bond et al. |
| 7,101,623 B2 | 9/2006 | Jordan et al. |
| 7,153,569 B2 | 12/2006 | Kaufman et al. |
| 7,193,032 B2 | 3/2007 | Culbert et al. |
| 7,241,838 B2 | 7/2007 | Shelby et al. |
| 7,368,503 B2 | 5/2008 | Hale |
| 7,468,335 B2 | 12/2008 | Imes et al. |
| 2002/0127939 A1 | 9/2002 | Hwo et al. |
| 2002/0168912 A1 | 11/2002 | Bond et al. |
| 2003/0022569 A1 | 1/2003 | Lee et al. |
| 2003/0022581 A1 | 1/2003 | Tsai et al. |
| 2003/0092343 A1 | 5/2003 | Bond et al. |
| 2003/0134915 A1 | 7/2003 | Scantlebury et al. |
| 2003/0176136 A1 | 9/2003 | Wadsworth |
| 2003/0191442 A1 | 10/2003 | Bewick-Sonntag et al. |
| 2004/0000313 A1 | 1/2004 | Gaynor et al. |
| 2004/0002273 A1 | 1/2004 | Fitting et al. |
| 2004/0053047 A1 | 3/2004 | Jackson et al. |
| 2004/0102123 A1 | 5/2004 | Bowen, Jr. et al. |
| 2004/0126578 A1* | 7/2004 | Tsai et al. ............ 428/373 |
| 2004/0132873 A1 | 7/2004 | Bailey et al. |
| 2005/0054999 A1 | 3/2005 | Morman et al. |
| 2005/0112350 A1 | 5/2005 | Ning |
| 2005/0112363 A1 | 5/2005 | Ning |
| 2005/0208294 A1 | 9/2005 | Kaufman et al. |
| 2007/0082573 A1 | 4/2007 | Noda et al. |
| 2007/0219339 A1 | 9/2007 | Fregoso-Infante et al. |

FOREIGN PATENT DOCUMENTS

| | | |
|---|---|---|
| EP | 0731198 A3 | 9/1996 |
| EP | 0905292 A1 | 3/1999 |
| EP | 1397536 B1 | 3/2004 |
| EP | 1397537 B1 | 3/2004 |
| EP | 1397538 B1 | 3/2004 |
| EP | 1397539 B1 | 3/2004 |
| JP | 7109659 | 4/1995 |
| JP | 7125128 | 5/1995 |
| JP | 11043857 | 2/1999 |
| JP | 11050369 | 2/1999 |
| JP | 11117164 | 4/1999 |
| JP | 11286864 | 10/1999 |
| JP | 2001172829 A | 6/2001 |
| JP | 2003064568 | 3/2003 |
| JP | 2003193349 A | 7/2003 |
| JP | 2005048350 A | 2/2005 |
| WO | WO 9850611 A1 | 11/1998 |
| WO | WO 02090629 A1 | 11/2002 |
| WO | WO 02090630 A1 | 11/2002 |
| WO | WO 2004061172 A2 | 7/2004 |
| WO | WO 2004061172 A3 | 7/2004 |
| WO | WO 2007070064 A1 | 6/2007 |
| WO | WO 2008008067 A1 | 1/2008 |
| WO | WO 2008008068 A1 | 1/2008 |
| WO | WO 2008008074 A1 | 1/2008 |
| WO | WO 2008073099 A1 | 6/2008 |

OTHER PUBLICATIONS

Abstract of Korean Patent No. KR1020030022514A, Mar. 17, 2003.
Abstract of Korean Patent No. KR1020040005193A, Jan. 16, 2004.
Abstract of Korean Patent No. KR1020040005194A, Jan. 16, 2004.
ASTM D 1117-97—*Standard Test Methods for Nonwoven Fabrics*, Mar. 10, 1997, pp. 311-313.
ASTM D 1238-04c—*Standard Test Method for Melt Flow Rates of Thermoplastics by Extrusion Plastometer*, current edition approved Dec. 1, 2004, originally approved in 1965, pp. 1-14.

ASTM D 1239-92—*Standard Test Method for Resistance of Plastic Films to Extraction by Chemicals*, current edition approved Aug. 15, 1992, pp. 281-282.

ASTM D 3418-03 (D 3417-99)—*Standard Test Method for Transition Temperatures and Enthalpies of Fusion and Crystallization of Polymers by Differential Scanning Calorimetry*, current edition approved Dec. 1, 2003, originally approved in 1975, pp. 66-72.

ASTM D 5034-95—*Standard Test Method for Breaking Strength and Elongation of Textile Fabrics (Grab Test)*, current edition approved May 15, 1995, pp. 674-681.

ASTM D 5338-92—*Standard Test Method for Determining Aerobic Biodegradation of Plastic Materials Under Controlled Composting Conditions*, current edition approved Dec. 15, 1992, pp. 456-461.

ASTM D 7191-05—*Standard Test Method for Determination of Moisture in Plastics by Relative Humidity Sensor*, current edition approved Nov. 1, 2005, pp. 1-4.

Article—*Biodegradation of aliphatic-aromatic copolyesters: evaluation of the final biodegradability and ecotoxicological impact of degradation intermediates*, Witt et al., Chemosphere 44, 2001, pp. 289-299.

Article—*Rheological Properties of Poly(lactides). Effect of Molecular Weight and Temperature on the Viscoelasticity of Poly(l-lactic acid)*, Cooper-White et al., Journal of Polymer Science: Part B: Polymer Physics, vol. 37, 1999, pp. 1803-1814.

Article—*Synthesis of Oligoester α,ω-diols by Alcoholysis of PET through the Reactive Extrusion Process*, Dannoux et al., The Canadian Journal of Chemical Engineering, vol. 80, Dec. 2002, pp. 1075-1082.

Product Information on Ecoflex® from BASF—The Chemical Company, Sep. 22, 2005, 4 pages.

Product Information from Ingeo and NatureWorks®—PLA Polymer 6201D, 6202D, and 6302D, 2005, 11 pages.

Search Report and Written Opinion for PCT/US2006/012049, Sep. 5, 2006, 15 pages.

Related U.S. Patent Applications.

\* cited by examiner

BIODEGRADABLE CONTINUOUS FILAMENT WEB

RELATED APPLICATIONS

The present application is a continuation-in-part application of International Application No. PCT/US2005/046178, filed in the United States Receiving Office on Dec. 15, 2005.

BACKGROUND OF THE INVENTION

Various attempts have been made to form nonwoven webs from biodegradable polymers. Although fibers prepared from biodegradable polymers are known, problems have been encountered with their use. For example, polylactic acid ("PLA") is one of the most common biodegradable and sustainable (renewable) polymers used to form nonwoven webs. Unfortunately, PLA nonwoven webs generally possess a low bond flexibility and high roughness due to the high glass transition temperature and slow crystallization rate of polylactic acid. In turn, thermally bonded PLA nonwoven webs often exhibit low elongations that are not acceptable in certain applications, such as in an absorbent article. Likewise, though polylactic acid may withstand high draw ratios, it requires high levels of draw energy to achieve the crystallization needed to overcome heat shrinkage. Other biodegradable polymers, such as polybutylene succinate (PBS), polybutylene adipate terephthalate (PBAT) and polycaprolactone (PCL), have a low glass transition temperature and softness characteristic similar to polyethylene. However, these polymers typically possess a small bonding window, which leads to difficulty in forming a nonwoven web from such polymers at high speeds.

As such, a need currently exists for a nonwoven web that is biodegradable and exhibits good mechanical properties.

SUMMARY OF THE INVENTION

In accordance with one embodiment of the present invention, a biodegredable nonwoven web is disclosed that comprises multicomponent filaments. The multicomponent filaments contain a first component and a second component. The first component contains a first aliphatic polyester having a melting point of from about 160° C. to about 250° C. and the second component contains a second aliphatic polyester. The melting point of the second aliphatic polyester is at least about 30° C. less than the melting point of the first aliphatic polyester. The second aliphatic polyester has a number average molecular weight of from about 30,000 to about 120,000 Daltons, a glass transition temperature of less than about 25° C., and an apparent viscosity of from about 50 to about 215 Pascal-seconds, as determined at a temperature of 160° C. and a shear rate of 1000 sec$^{-1}$.

In accordance with another embodiment of the present invention, a biodegradable nonwoven web is disclosed that comprises substantially continuous multicomponent filaments. The filaments comprise a first component and a second component, the first component containing a first aliphatic polyester and the second component containing a second aliphatic polyester. The melting point of the first component is from about 160° C. to about 250° C. and the melting point of the second component is at least about 30° C. less than the melting point of the first component. The second aliphatic polyester has a number average molecular weight of from about 30,000 to about 120,000 Daltons, a glass transition temperature of less than about 25° C., and an apparent viscosity of from about 50 to about 215 Pascal-seconds, as determined at a temperature of 160° C. and a shear rate of 1000 sec$^{-1}$.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
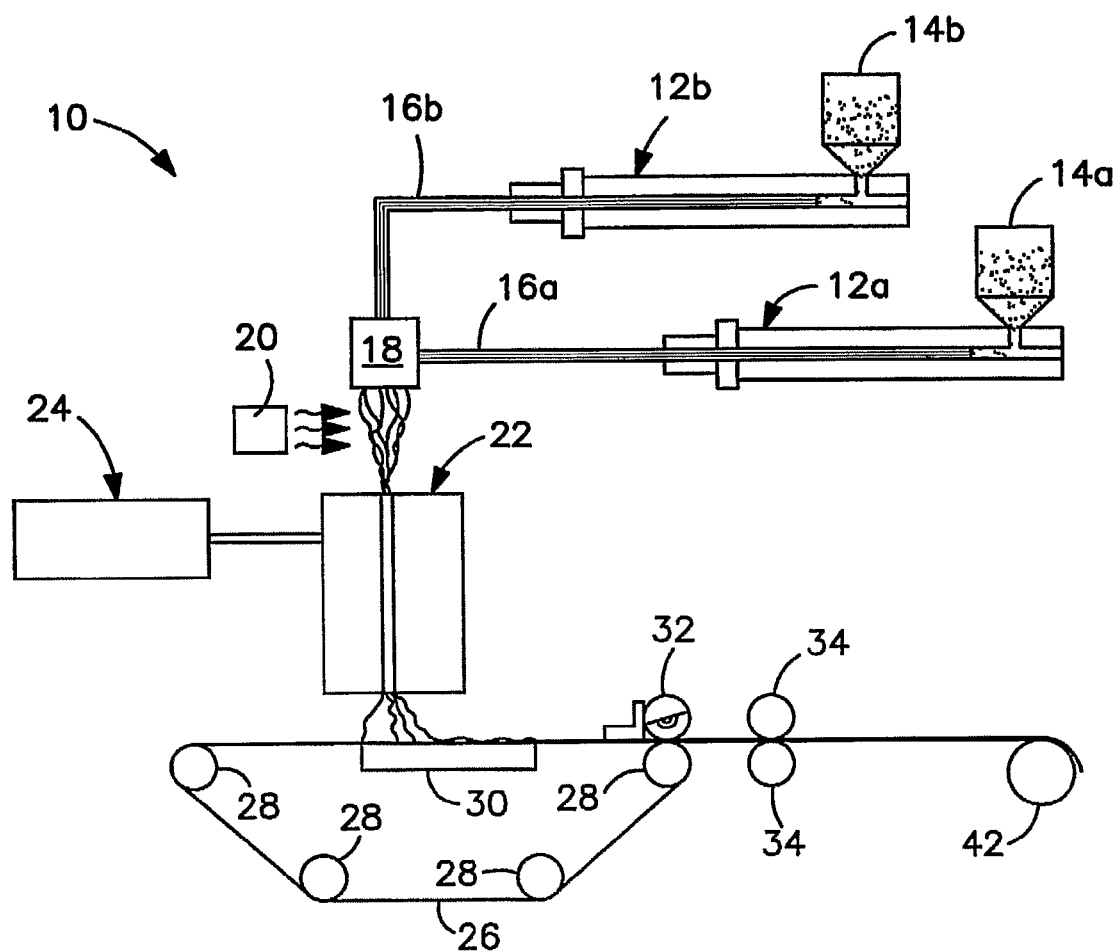
FIG. 1 is a schematic illustration of a process that may be used in one embodiment of the present invention to form a nonwoven web.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Definitions

As used herein, the term "biodegradable" or "biodegradable polymer" generally refers to a material that degrades from the action of naturally occurring microorganisms, such as bacteria, fungi, and algae; environmental heat; moisture; or other environmental factors. The biodegradability of a material may be determined using ASTM Test Method 5338.92.

As used herein, the term "continuous filament web" generally refers to a nonwoven web containing substantially continuous filaments. The filaments may, for example, have a length much greater than their diameter, such as a length to diameter ratio ("aspect ratio") greater than about 15,000 to 1, and in some cases, greater than about 50,000 to 1.

As used herein, the term "nonwoven web" refers to a web having a structure of individual threads (e.g., fibers or filaments) that are randomly interlaid, not in an identifiable manner as in a knitted fabric. Nonwoven webs include, for example, meltblown webs, spunbond webs, carded webs, wet-laid webs, airlaid webs, coform webs, hydraulically entangled webs, etc. The basis weight of the nonwoven web may generally vary, but is typically from about 5 grams per square meter ("gsm") to 200 gsm, in some embodiments from about 10 gsm to about 150 gsm, and in some embodiments, from about 15 gsm to about 100 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous filaments. The filaments are formed by extruding a molten thermoplastic material from a plurality of fine, usually circular, capillaries of a spinnerette with the diameter of the extruded filaments then being rapidly reduced as by, for example, eductive drawing and/or other well-known spunbonding mechanisms. The production of spunbond webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond filaments are generally not tacky when they are deposited onto a collecting surface. Spunbond filaments may sometimes have diameters less than about 40 micrometers, and are often between about 5 to about 20 micrometers.

As used herein, the term "multicomponent" refers to filaments formed from at least two polymer components (e.g., bicomponent filaments).

DETAILED DESCRIPTION

The present invention is directed to a continuous filament nonwoven web that is biodegradable. The filaments are multicomponent and contain a first component formed from at least one high-melting aliphatic polyester and a second component formed from at least one low-melting aliphatic polyester. The first and second components may be arranged in any desired configuration to form the multicomponent filaments in accordance with the present invention. The configuration of such materials may be, for example, a sheath-core, side-by-side, pie, island-in-the-sea, and so forth. The resulting multicomponent, melt-spun filaments are substantially biodegradable, yet readily processed into fibrous structures that exhibit good mechanical properties.

I. First Component

As stated, the first component of the multicomponent filaments is formed from one or more "high melting point" biodegradable aliphatic polyesters. Typically, the melting point of such polyesters is from about 160° C. to about 250° C., in some embodiments from about 170° C. to about 240° C., and in some embodiments, from about 180° C. to about 220° C. Various "high melting point" aliphatic polyesters may be employed in the present invention, such as polyesteramides, modified polyethylene terephthalate, polylactic acid (PLA), terpolymers based on polylactic acid, polyglycolic acid, polyalkylene carbonates (such as polyethylene carbonate), polyhydroxyalkanoates (PHA), polyhydroxybutyrates (PHB), polyhydroxyvalerates (PHV), and polyhydroxybutyrate-hydroxyvalerate copolymers (PHBV). The term "polylactic acid" generally refers to homopolymers of lactic acid, such as poly(L-lactic acid), poly(D-lactic acid), poly(DL-lactic acid), mixtures thereof, and copolymers containing lactic acid as the predominant component and a small proportion of a copolymerizable comonomer, such as 3-hydroxybutyrate, caprolactone, glycolic acid, etc.

Any known polymerization method, such as polycondensation or ring-opening polymerization, may be used to polymerize lactic acid. In the polycondensation method, for example, L-lactic acid, D-lactic acid, or a mixture thereof is directly subjected to dehydro-polycondensation. In the ring-opening polymerization method, a lactide that is a cyclic dimer of lactic acid is subjected to polymerization with the aid of a polymerization-adjusting agent and catalyst. The lactide may include L-lactide (a dimer of L-lactic acid), D-lactide (a dimer of D-lactic acid), DL-lactide (a condensate of L-lactic acid and D-lactic acid), or mixtures thereof. These isomers may be mixed and polymerized, if necessary, to obtain polylactic acid having any desired composition and crystallinity. A small amount of a chain-extending agent (e.g., a diisocyanate compound, an epoxy compound or an acid anhydride) may also be employed to increase the molecular weight of the polylactic acid. Generally speaking, the weight average molecular weight of the polylactic acid is within the range of about 60,000 to about 1,000,000. One particularly suitable polylactic acid polymer that may be used in the present invention is commercially available from Biomer, Inc. (Germany) under the name Biomer™ L9000. Still other suitable polylactic acid polymers are commercially available from Natureworks, LLC of Minneapolis, Minn.

Although not required, the high melting point aliphatic polyesters typically constitute the principal ingredient of the first component. That is, the aliphatic polyesters may constitute at least about 90 wt. %, in some embodiments at least about 92 wt. %, and in some embodiments, at least about 95 wt. % of the first component. In such embodiments, the characteristics of the first component (e.g., melting point) will be substantially the same as the characteristics of the aliphatic polyesters employed. For example, the melting point of the first component may range from about 160° C. to about 250° C., in some embodiments from about 170° C. to about 240° C., and in some embodiments, from about 180° C. to about 220° C.

II. Second Component

The second component is formed from one or more "low melting point" biodegradable aliphatic polyesters. Typically, such polyesters have a melting point of from about 50° C. to about 160° C., in some embodiments from about 80° C. to about 160° C., and in some embodiments, from about 100° C. to about 140° C. Moreover, the melting point is also typically at least about 30° C., in some embodiments at least about 40° C., and in some embodiments, at least about 50° C. less than the melting point of the "high melting point" aliphatic polyesters. "Low melting point" aliphatic polyesters are useful in that they biodegrade at a faster rate than the high melting point polyesters. In addition, they are generally softer to the touch than most "high melting point" aliphatic polyesters. The glass transition temperature ("$T_g$") of the low melting point polyesters may also be less than that of the high melting point polyesters to improve flexibility and processability of the polymers. For example, the low melting point aliphatic polyesters may have a $T_g$ of about 25° C. or less, in some embodiments about 0° C. or less, and in some embodiments, about −10° C. or less. Such a glass transition temperature may be at least about 5° C., in some embodiments at least about 10° C., and in some embodiments, at least about 15° C. less than the glass transition temperature of the high melting point polyesters.

Examples of aliphatic polyesters that may have a low melting point and glass transition temperature include aliphatic polyesters with repeating units of at least 5 carbon atoms (e.g., polyhydroxyvalerate, polyhydroxybutyrate-hydroxyvalerate copolymer and polycaprolactone), and succinate-based aliphatic polymers (e.g., polybutylene succinate, polybutylene succinate adipate, and polyethylene succinate). More specific examples may include polyethylene oxalate, polyethylene malonate, polyethylene succinate, polypropylene oxalate, polypropylene malonate, polypropylene succinate, polybutylene oxalate, polybutylene malonate, polybutylene succinate, and blends and copolymers of these compounds. Among these compounds, polybutylene succinate and copolymers thereof are normally preferred.

Aliphatic polyesters are typically synthesized through the condensation polymerization of a polyol and an aliphatic dicarboxylic acid or an anhydride thereof. The polyols may be substituted or unsubstituted, linear or branched, polyols selected from polyols containing 2 to about 8 carbon atoms, polyalkylene ether glycols containing 2 to 8 carbon atoms, and cycloaliphatic diols containing about 4 to about 12 carbon atoms. Substituted polyols typically contain 1 to about 4 substituents independently selected from halo, $C_6$-$C_{10}$ aryl and $C_1$-$C_4$ alkoxy. Examples of polyols that may be used include, but are not limited to, ethylene glycol, diethylene glycol, propylene glycol, 1,3-propanediol, 2,2-dimethyl-1,3-propanediol, 1,3-butanediol, 1,4-butanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, and tetraethylene glycol. Preferred polyols include 1,4-butanediol; 1,3-propanediol; ethylene glycol; 1,6-hexanediol; diethylene glycol; and 1,4-cyclohexanedimethanol. Representative aliphatic dicarboxylic acids that may be used include substituted or unsubstituted, linear or branched, non-aromatic dicarboxylic acids selected from aliphatic dicarboxylic acids containing 2 to about 12 carbon atoms and cycloaliphatic dicarboxylic acids containing about 5 to about 10 carbon atoms. The substituted non-aromatic dicarboxylic acids will typically contain 1 to about 4 substituents selected from halo, $C_6$-$C_{10}$ aryl, and $C_1$-$C_4$ alkoxy. Non-limiting examples of aliphatic and cycloaliphatic dicarboxylic acids include malonic, succinic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. The polymerization is catalyzed by a catalyst, such as a titanium-based catalyst (e.g., tetraisopropyltitanate, tetraisopropoxy titanium, dibutoxydiacetoacetoxy titanium, or tetrabutyltitanate).

If desired, a diisocyanate chain extender may be reacted with the aliphatic polyester prepolymer to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri- or polyisocyanates. The preferred diisocyanate is hexamethylene diisocyanate. The amount of the chain extender employed is typically from about 0.3 to about 3.5 wt. %, in some embodiments, from about 0.5 to about 2.5 wt. % based on the total weight percent of the polymer.

The aliphatic polyesters may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, glycerol, 1,2,4-butanetriol, pentaerythritol, 1,2,6-hexanetriol, sorbitol, 1,1,4,4,-tetrakis(hydroxymethyl) cyclohexane, tris(2-hydroxyethyl)isocyanurate, and dipentaerythritol. Representative higher molecular weight polyols (molecular weight of 400 to 3000) that may be used as branching agents include triols derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethanetetracarboxylic acid, 1,1,2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

Polycaprolactone polymers may also be used in the present invention. Polycaprolactone polymers are generally prepared by the polymerization of ϵ-caprolactone, which is a seven-member ring compound that is characterized by its reactivity. Cleavage usually takes place at the carbonyl group. Higher molecular weight polycaprolactone may be prepared under the influence of a wide variety of catalysts, such as aluminum alkyls, organometallic compositions, such as Group IA, IIA, IIB, or IIIA metal alkyls, Grignard reagents, Group II metal dialkyls, calcium or other metal amides or alkyl amides, reaction products of alkaline earth hexamoniates, alkaline oxides and acetonitrile, aluminum trialkoxides, alkaline earth aluminum or boron hydrides, alkaline metal or alkaline earth hydrides or alkaline metals alone. An initiator may also be used in the preparation of polycaprolactone, such as an aliphatic diol that forms a terminal end group. Examples of polycaprolactone polymers that may be suitable for use in the present invention include a variety of polycaprolactone polymers that are available from Union Carbide Corporation, Somerset, N.J., under the designation TONE™ Polymer P767E and TONE™ Polymer P787 polycaprolactone polymers.

The low melting point aliphatic polyesters described above are primarily aliphatic in nature, i.e., the monomer constituents are primarily aliphatic, to optimize biodegradability. For example, the low melting point aliphatic polyesters typically contain at least about 50 mol. %, in some embodiments at least about 60 mol. %, and in some embodiments, at least about 70 mol. % of aliphatic monomer(s). Although primarily aliphatic in nature, the low melting point polyesters may nevertheless contain a minor portion of other monomer constituents, such as aromatic monomers (e.g., terephtalic acid) that further improve the strength and tenacity of the filaments. When utilized, the aromatic monomers may, for example, constitute from about 1 mol. % to about 50 mol. %, in some embodiments from about 10 mol. % to about 40 mol. %, and in some embodiments, from about 15 mol. % to about 30 mol. % of the low melting point aliphatic polyester. One particular example of an aliphatic polyester containing an aromatic terephtalic acid monomer (~22 mol. %) constituent is available under the designation Ecoflex™ F BX 7011 from BASF Corp. Another example of an aliphatic polyester containing an aromatic terephtalic acid monomer (~25 mol. %) constituent is available under the designation Enpol™ 8060M from IRE Chemicals (South Korea).

Regardless of their particular type, the present inventors have discovered that "low melting point" aliphatic polyesters having a certain combination of thermal and mechanical properties may provide improved processability and strength to the resulting multicomponent filaments. For example, aliphatic polyesters having too great of a molecular weight generally possess heavily entangled polymer chains and thus result in a thermoplastic composition that is difficult to process. Conversely, aliphatic polyesters having too low of a molecular weight do not generally possess enough entanglement, which leads to a relatively weak melt strength. Thus, the "low melting point" aliphatic polyesters employed in the present invention typically have a number average molecular weight ("$M_n$") ranging from about 30,000 to about 120,000 Daltons, in some embodiments from about 40,000 to about 100,000 Daltons, and in some embodiments, from about 45,000 to about 85,000 Daltons. Likewise, the "low melting point" aliphatic polyesters also typically have a weight average molecular weight ("$M_w$") ranging from about 30,000 to about 240,000 Daltons, in some embodiments from about 50,000 to about 190,000 Daltons, and in some embodiments, from about 60,000 to about 105,000 Daltons. The molecular weight distribution of the selected polymers is also relatively narrow to enhance polymer processing and provide more consistent properties. That is, the ratio of the weight average molecular weight to the number average molecular weight ("$M_w/M_n$"), i.e., the "polydispersity index", is relatively low. For example, the polydispersity index typically ranges from about 1.0 to about 3.0, in some embodiments from about 1.2 to about 2.0, and in some embodiments, from about 1.4 to about 1.8. The weight and number average molecular weights may be determined by methods known to those skilled in the art.

To provide improved processability, the "low melting point" aliphatic polyester is also selected to have an apparent viscosity within a certain range. More specifically, aliphatic polyesters having too great of an apparent viscosity will generally be difficult to process. On the other hand, aliphatic polyesters having too low of an apparent viscosity will generally result in an extruded filament lacking tensile strength and sufficient bonding capacity. Thus, in most embodiments, the "low melting point" aliphatic polyester has an apparent viscosity of from about 50 to about 215 Pascal seconds (Pa·s), in some embodiments from about 75 to about 200 Pa·s, and in some embodiments, from about 80 to about 150 Pa·s, as determined at a temperature of 160° C. and a shear rate of 1000 $sec^{-1}$. The present inventors have discovered that the particular combination of molecular weight and viscosity set forth above results in polymers having enhanced processability without adversely affecting the strength and bonding capacity of the resulting filament.

The melt flow index of the "low melting point" aliphatic polyesters may also be selected within a certain range to optimize the properties of the resulting filaments. The melt flow index is the weight of a polymer (in grams) that may be forced through an extrusion rheometer orifice (0.0825-inch diameter) when subjected to a force of 2160 grams in 10 minutes at 190° C. Generally speaking, the melt flow index is high enough to improve melt processability, but not so high as to adversely interfere with the binding properties of the filaments. Thus, in most embodiments of the present invention, the "low melting point" aliphatic polyesters have a melt flow index of from about 5 to about 200 grams per 10 minutes, in some embodiments from about 15 to about 160 grams per 10 minutes, and in some embodiments, from about 20 to about 120 grams per 10 minutes, measured in accordance with ASTM Test Method D1238-E.

The crystallinity of the aliphatic polyester also influences the properties of the resulting multicomponent filaments. That is, polymers having a higher degree of melt and crystallization enthalpy are more readily incorporated into bonded web products. For example, such polymers are more readily able to bond at higher speeds and also have a lower degree of shrinkage, thereby improving web stability, tensile strength, and web aesthetics. Thus, the aliphatic polyesters are typically selected to have a degree of crystallinity or latent heat of fusion ($\Delta H_f$) of greater than about 25 Joules per gram ("J/g"), in some embodiments greater than about 35 J/g, and in some embodiments, greater than about 50 J/g. Likewise, the aliphatic polyesters are also typically selected to have a latent heat of crystallinity ($\Delta H_c$) of greater than about 35 Joules per gram ("J/g"), in some embodiments greater than about 50 J/g, and in some embodiments, greater than about 60 J/g.

One difficulty encountered in the thermal processing of aliphatic polyester polymers into filaments is the sticky nature of these polymers. Attempts to draw the filaments, either mechanically, or through an air drawing process, will often result in the aggregation of the filaments into a solid mass. Thus, in accordance with the present invention, the "low melting point" aliphatic polyesters are also selected to have a relatively high crystallization temperature ("$T_c$"), thereby reducing tackiness. Specifically, the crystallization temperature may range from about 40° C. to about 100° C., in some embodiments from about 50° C. to about 90° C., and in some embodiments, from about 60° C. to about 80° C. As discussed in more detail below, the latent heat of fusion ($\Delta H_f$), latent heat of crystallization ($\Delta H_c$), and crystallization temperature may all be determined using differential scanning calorimetry ("DSC") in accordance with ASTM D-3417.

Any of a variety of "low melting point" aliphatic polyester polymers may possess the desired thermal and mechanical properties referenced above. In particular embodiments of the present invention, for instance, polybutylene succinate copolyesters are employed as the second component of the multicomponent filaments. One specific example of a suitable polybutylene succinate polymers is commercially available from IRE Chemicals (South Korea) under the designation Enpol™ G4500.

A beneficial aspect of the present invention is that the above-described thermal and mechanical properties of the "low melting point" aliphatic polyesters may be provided without the need for conventional additives. For example, many conventional biodegradable thermoplastic compositions require the use of a nucleating agent to improve processing and to facilitate crystallization during quenching. One type of such a nucleating agent is a multi-carboxylic acid, such as succinic acid, glutaric acid, adipic acid, pimelic acid, suberic acid, azelaic acid, sebacic acid, and mixtures of such acids, as described in U.S. Pat. No. 6,177,193 to Tsai, et al. The present inventors have discovered, however, that through the careful selection of an aliphatic polyester having certain thermal and physical properties, such nucleating agents are not necessarily required. In fact, the present inventors have discovered that excellent results may be achieved using aliphatic polyesters as the principal ingredient of the second component. That is, the aliphatic polyesters may constitute at least about 90 wt. %, in some embodiments at least about 92 wt. %, and in some embodiments, at least about 95 wt. % of the second component. In such embodiments, the characteristics of the second component (e.g., melting point, glass transition temperature, apparent viscosity, molecular weight, etc.) will be substantially the same as the characteristics of the aliphatic polyesters employed. For example, the melting point of the second component may be at least about 30° C., in some embodiments at least about 40° C., and in some embodiments, at least about 50° C. less than the melting point of the first component, and likewise range from about 50° C. to about 160° C., in some embodiments from about 80° C. to about 160° C., and in some embodiments, from about 100° C. to about 140° C. Nevertheless, it should be understood that nucleating agents may be used in some embodiments of the present invention. When utilized, however, the nucleating agents are typically present in an amount of less than about 0.5 wt. %, in some embodiments less than about 0.25 wt. %, and in some embodiments, less than about 0.1 wt. % of the second component.

Although aliphatic polyesters are the primary ingredient of the second component, other ingredients may of course be utilized the second component for a variety of different reasons. For instance, a wetting agent may be employed in some embodiments of the present invention to improve the hydrophilicity of the resulting filaments. Wetting agents suitable for use in the present invention are generally compatible with the aliphatic polyesters. Examples of suitable wetting agents may include surfactants, such as UNITHOX® 480 and UNITHOX® 750 ethoxylated alcohols, or UNICID™ acid amide ethoxylates, all available from Petrolite Corporation of Tulsa, Okla. Other suitable wetting agents are described in U.S. Pat. No. 6,177,193 to Tsai, et al., which is incorporated herein in its entirety by reference thereto for all relevant purposes. Still other materials that may be used include, without limitation, pigments, antioxidants, stabilizers, surfactants, waxes, flow promoters, solid solvents, plasticizers, particulates, and other materials added to enhance the processability of the thermoplastic composition. When utilized, it is normally desired that the amounts of these additional ingredients are minimized to ensure optimum compatibility and cost-effectiveness. Thus, for example, it is normally desired that such ingredients constitute less than about 10 wt. %, in some embodiments less than about 8 wt. %, and in some embodiments, less than about 5 wt. % of the second component.

III. Continuous Filament Webs

The multicomponent filaments of the present invention may constitute the entire fibrous component of the continuous filament web or blended with other types of fibers (e.g., staple fibers, filaments, etc). For example, additional monocomponent and/or multicomponent synthetic fibers may be utilized in the nonwoven web. Some suitable polymers that may be used to form the synthetic fibers include, but are not limited to: polyolefins, e.g., polyethylene, polypropylene, polybutylene, and the like; polytetrafluoroethylene; polyesters, e.g., polyethylene terephthalate and the like; polyvinyl acetate; polyvinyl chloride acetate; polyvinyl butyral; acrylic resins, e.g., polyacrylate, polymethylacrylate, polymethylmethacrylate, and the like; polyamides, e.g., nylon; polyvinyl chloride; polyvinylidene chloride; polystyrene; polyvinyl alcohol; polyurethanes; polylactic acid; and the like. If desired, biodegradable polymers, such as poly(glycolic acid) (PGA), poly(lactic acid) (PLA), poly(β-malic acid) (PMLA), poly(ε-caprolactone) (PCL), poly(ρ-dioxanone) (PDS), and poly(3-hydroxybutyrate) (PHB). Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. When blended with other types of fibers, it is normally desired that the multicomponent filaments of the present invention constitute from about 20 wt % to about 95 wt. %, in some embodiments from about 30 wt. % to about 90 wt. %, and in some embodiments, from about 40 wt. % to about 80 wt. % of the total amount of fibers employed in the web.

Any of a variety of known techniques may be employed to form the continuous filament web in accordance with the present invention. Typically, the components are extruded in separate extruders, but they may also be spun together. Referring to FIG. 1, for example, one embodiment of a process 10 for forming a continuous filament web in accordance with the present invention is shown. As illustrated, the process 10 of this embodiment is arranged to produce a bicomponent, continuous filament web, although it should be understood that other embodiments are contemplated by the present invention. The process 10 employs a pair of extruders 12a and 12b for separately extruding a first component A (i.e., "high melting point" polymer component) and a second component B (i.e., "high melting point" polymer component). The relative amount of the components A and B may generally vary based on the desired properties. For example, the first component A may constitute from about 5 wt. % to about 95 wt. %, in some embodiments from about 10 wt. % to about 90 wt. %, and in some embodiments, from about 15 wt. % to about 85 wt. % of the multicomponent filaments. Likewise, the second component B may constitute from about 5 wt. % to about 95 wt. %, in some embodiments from about 10 wt. % to about 90 wt. %, and in some embodiments, from about 15 wt. % to about 85 wt. % of the multicomponent filaments.

The first component A is fed into the respective extruder 12a from a first hopper 14a and the second component B is fed into the respective extruder 12b from a second hopper 14b. The components A and B are fed from the extruders 12a and 12b ("co-extruded") through respective polymer conduits 16a and 16b to a spinneret 18. Spinnerets for extruding multicomponent filaments are well known to those of skill in the art. For example, the spinneret 18 may include a housing containing a spin pack having a plurality of plates stacked one on top of each other and having a pattern of openings arranged to create flow paths for directing polymer components A and B separately through the spinneret 18. The spinneret 18 also has openings arranged in one or more rows. The openings form a downwardly extruding curtain of filaments when the polymers are extruded therethrough. The spinneret 18 may be arranged to form sheath/core, side-by-side, pie, or other configurations.

The process 10 also employs a quench blower 20 positioned adjacent the curtain of filaments extending from the spinneret 18. Air from the quench air blower 20 quenches the filaments extending from the spinneret 18. The quench air may be directed from one side of the filament curtain as shown in FIG. 1 or both sides of the filament curtain. A fiber draw unit or aspirator 22 is positioned below the spinneret 18 and receives the quenched filaments. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255, which are incorporated herein in their entirety by reference thereto for all relevant purposes. The fiber draw unit 22 generally includes an elongate vertical passage through which the filaments are drawn by aspirating air entering from the sides of the passage and flowing downwardly through the passage. A heater or blower 24 supplies aspirating air to the fiber draw unit 22. The aspirating air draws the filaments and ambient air through the fiber draw unit 22. Thereafter, the filaments are formed into a coherent web structure by randomly depositing the filaments onto a forming surface 26 (optionally with the aid of a vacuum) and then bonding the resulting web using any known technique.

To initiate filament formation, the hoppers 14a and 14b are initially filled with the respective components A and B. Components A and B are melted and extruded by the respective extruders 12a and 12b through polymer conduits 16a and 16b and the spinneret 18. Due to the relatively low apparent viscosity of the aliphatic polyesters used in the present invention, lower extrusion temperatures may be employed. For example, the extruder 12b for Component B ("low melting point" polyester) may employ one or multiple zones operating at a temperature of from about 120° C. to about 200° C., and in some embodiments, from about 145° C. to about 195° C. Likewise, the extruder 12a for Component A ("high melting point" polyester) may employ one or multiple zones operating at a temperature of from about 160° C. to about 250° C., and in some embodiments, from about 190° C. to about 225° C. Typical shear rates range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$.

As the extruded filaments extend below the spinneret 18, a stream of air from the quench blower 20 at least partially quenches the filaments. Such a process generally reduces the temperature of the extruded polymers at least about 100° C. over a relatively short time frame (seconds). This will generally reduce the temperature change needed upon cooling, to preferably be less than 150° C. and, in some cases, less than 100° C. The ability to use relatively low extruder temperature in the present invention also allows for the use of lower quenching temperatures. For example, the quench blower 20 may employ one or more zones operating at a temperature of from about 20° C. to about 100° C., and in some embodiments, from about 25° C. to about 60° C. After quenching, the filaments are drawn into the vertical passage of the fiber draw unit 22 by a flow of a gas such as air, from the heater or blower 24 through the fiber draw unit. The flow of gas causes the filaments to draw or attenuate which increases the molecular orientation or crystallinity of the polymers forming the filaments. The filaments are deposited through the outlet opening of the fiber draw unit 22 and onto a foraminous surface 26. Due to the high strength of the filaments of the present invention, high draw ratios (e.g., linear speed of the foraminous surface 26 divided by the melt pump rate of the extruders 12a and 12b) may be employed in the present invention. For example, the draw ratio may be from about 200:1 to about 6000:1, in some embodiments from about 500:1 to about 5000:1, and in some embodiments, from about 1000:1 to about 4000:1.

The desired denier of the filaments may vary depending on the desired application. Typically, the filaments are formed to have a denier per filament of less than about 6, in some embodiments less than about 3, and in some embodiments, from about 0.5 to about 3. In addition, the filaments generally have an average diameter not greater than about 100 microns, in some embodiments from about 0.5 microns to about 50 microns, and in some embodiments, from about 4 microns to about 40 microns.

An endless foraminous forming surface 26 is positioned below the fiber draw unit 22 and receives the filaments from an outlet opening. The forming surface 26 travels around guide rollers 28. A vacuum 30 positioned below the forming surface 26 to draw the filaments against the forming surface 26 and consolidate the unbonded nonwoven web. The web may then be compressed by a compression roller 32.

Once formed, the nonwoven web is then bonded using any conventional technique, such as with an adhesive or autogenously (e.g., fusion and/or self-adhesion of the filaments without an applied external adhesive). Autogenous bonding, for instance, may be achieved through contact of the filaments while they are semi-molten or tacky, or simply by blending a tackifying resin and/or solvent with the aliphatic polyester(s) used to form the filaments. Suitable autogenous bonding techniques may include ultrasonic bonding, thermal bonding, through-air bonding, and so forth.

In FIG. 1, for instance, the web passes through a nip formed between a pair of rolls 34, one or both of which are heated to melt-fuse the filaments. One or both of the rolls 34 may also contain intermittently raised bond points to provide an intermittent bonding pattern. The pattern of the raised points is generally selected so that the nonwoven web has a total bond area of less than about 50% (as determined by conventional optical microscopic methods), and in some embodiments, less than about 30%. Likewise, the bond density is also typically greater than about 100 bonds per square inch, and in some embodiments, from about 250 to about 500 pin bonds per square inch. Such a combination of total bond area and bond density may be achieved by bonding the web with a pin bond pattern having more than about 100 pin bonds per square inch that provides a total bond surface area less than about 30% when fully contacting a smooth anvil roll. In some embodiments, the bond pattern may have a pin bond density from about 250 to about 350 pin bonds per square inch and a total bond surface area from about 10% to about 25% when contacting a smooth anvil roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown, which are incorporated herein in their entirety by reference thereto for all purposes.

Due to the particular rheological and thermal properties of the components used to form the multicomponent filaments, the web bonding conditions (e.g., temperature and nip pressure) may be selected to cause the low melting point aliphatic polyester to melt and flow without substantially melting the high melting point aliphatic polyester. For example, the bonding temperature (e.g., the temperature of the rollers 34) may be from about 50° C. to about 160° C., in some embodiments from about 80° C. to about 160° C., and in some embodiments, from about 100° C. to about 140° C. Likewise, the nip pressure may range from about 5 to about 150 pounds per square inch, in some embodiments, from about 10 to about 100 pounds per square inch, and in some embodiments, from about 30 to about 60 pounds per square inch.

When bonded in this manner, the low melting point polymer may thus form a matrix within the compacted area that substantially surrounds the high melting point polymer. Because the high melting point polymer does not substantially melt, however, it retains a substantially fibrous form. The high melting point polymer is also generally oriented within the compacted area in two or more directions due to the random manner in which the filaments are deposited. One polymer, for instance, may be oriented from about 60° to about 120°, and in some cases, about 90°, relative to another polymer within a compacted area. In this manner, the high melting point polymer may impart enhanced strength and toughness to the resulting web. For example, the nonwoven web of the present invention may exhibit a relatively high "peak load", which indicates the maximum load to break as expressed in units of grams-force per inch. The MD peak load of the web may, for instance, be at least about 3000 grams-force per inch ("$g_f$/in"), in some embodiments at least about 3500 $g_f$/in, and in some embodiments, at least about 4000 $g_f$/in. The CD peak load may also be at least about 1200 grams-force per inch ("$g_f$/in"), in some embodiments at least about 1500 $g_f$/in, and in some embodiments, at least about 2500 $g_f$/in.

In addition to contributing to the overall strength of the web, the selected bond conditions may also improve other mechanical properties of the web. For example, although retaining its fiber form within a compacted area, the high melting point polymer will normally release or separate from the compacted area upon the application of strain, rather than fracture. By releasing under strain, the polymer may continue to function as a load bearing member even after the web has exhibited substantial elongation. In this regard, the nonwoven web of the present invention is capable of exhibiting improved "peak elongation" properties, i.e., the percent elongation of the web at its peak load. For example, the nonwoven web of the present invention may exhibit a machine direction ("MD") peak elongation of at least about 10%, in some embodiments at least about 20%, and in some embodiments, at least about 35%. The nonwoven web may also exhibit a cross-machine direction ("CD") peak elongation of at least about 35%, in some embodiments at least about 45%, and in some embodiments, at least about 50%. Of course, in addition to possessing good mechanical properties, the nonwoven web of the present invention is also soft, drapable, and tactile. Further, the nonwoven web possesses good water absorption characteristics, which facilitates its ability to be used in absorbent articles.

The nonwoven web of the present invention may be used in a wide variety of applications. For example, as indicated above, the nonwoven web may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. In one particular embodiment, the nonwoven web is used to form an outer cover of an absorbent article. For example, a breathable film may be laminated to a nonwoven web formed according to the present invention.

Figure 7:
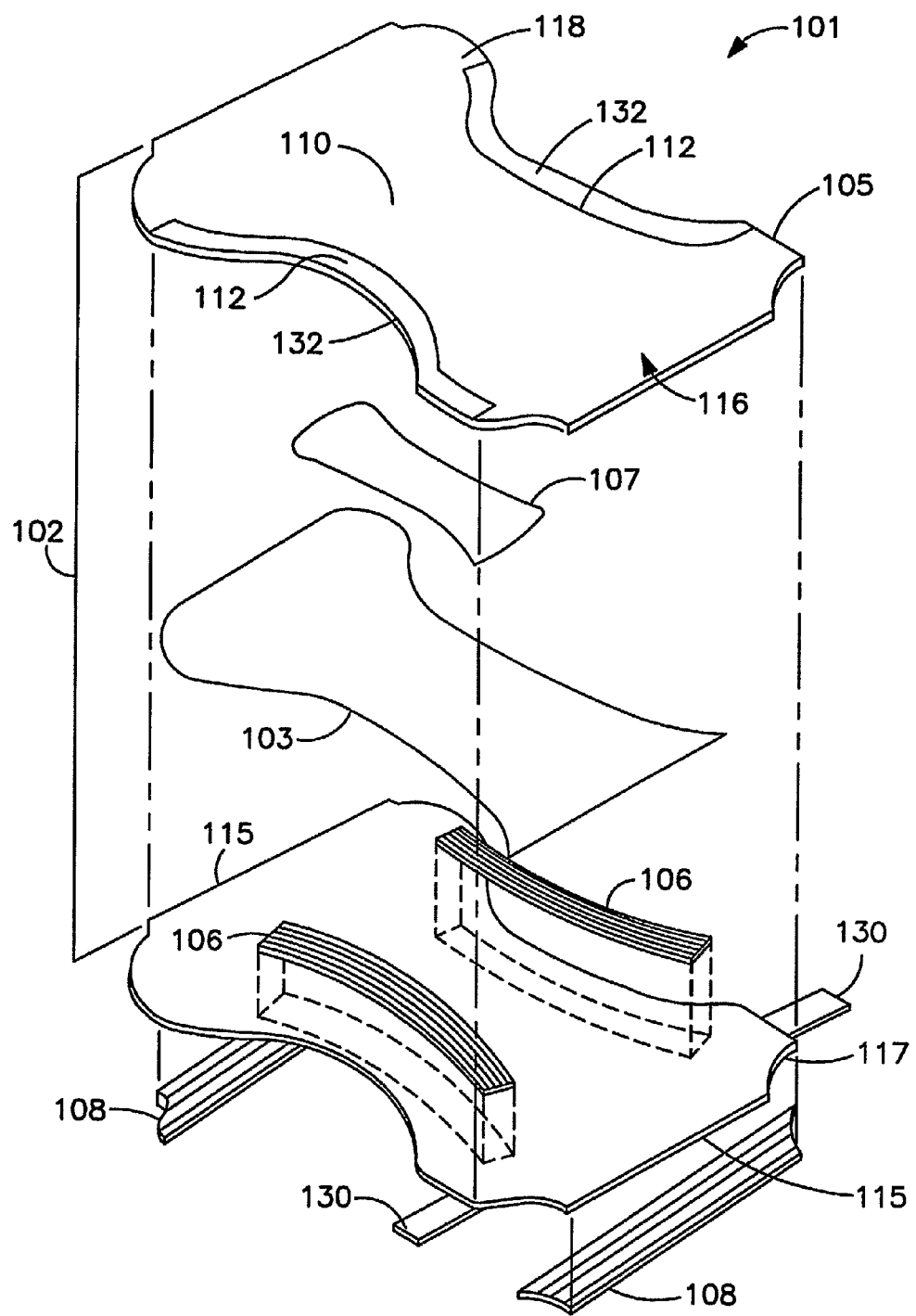
FIG. 7 is a perspective view of an absorbent article that may be formed according to one embodiment of the present invention.

Various embodiments of an absorbent article that may be formed according to the present invention will now be described in more detail. For purposes of illustration only, an absorbent article is shown in FIG. 7 as a diaper 101. However, as noted above, the invention may be embodied in other types of absorbent articles, such as incontinence articles, sanitary napkins, diaper pants, feminine napkins, children's training pants, and so forth. In the illustrated embodiment, the diaper 101 is shown as having an hourglass shape in an unfastened configuration. However, other shapes may of course be utilized, such as a generally rectangular shape, T-shape, or I-shape. As shown, the diaper 101 includes a chassis 102 formed by various components, including an outer cover 117, bodyside liner 105, absorbent core 103, and surge layer 107. It should be understood, however, that other layers may also be used in the present invention. Likewise, one or more of the layers referred to in FIG. 7 may also be eliminated in certain embodiments of the present invention.

The outer cover 117 is typically formed from a material that is substantially impermeable to liquids. For example, the outer cover 117 may be formed from a thin plastic film or other flexible liquid-impermeable material. In one embodiment, the outer cover 117 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 may be formed from a polyolefin film laminated to a nonwoven web. For example, a stretch-thinned polypropylene film having a thickness of about 0.015 millimeter may be thermally laminated to a spunbond web of polypropylene filaments. If desired, the nonwoven web of the present invention may be used to form the outer cover 117.

The diaper 101 also includes a bodyside liner 105. The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. The liner 105 may be liquid-permeable to permit liquid to readily penetrate through its thickness. In one particular embodiment, the liner includes a nonwoven web formed in accordance with the present invention. Exemplary liner constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941, all of which are incorporated herein in their entirety by reference thereto for all purposes.

As illustrated in FIG. 7, the diaper 101 may also include a surge layer 107 that helps to decelerate and diffuse surges or gushes of liquid that may be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 may be located on an outwardly facing surface 118 of the bodyside liner 105. The surge layer 107 is typically constructed from highly liquid-permeable materials. Suitable materials may include porous woven materials, porous nonwoven materials, and apertured films. In one particular embodiment, the surge layer 107 includes a nonwoven web formed according to the present invention. Other examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

Besides the above-mentioned components, the diaper 101 may also contain various other components as is known in the art. For example, the diaper 101 may also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 103. The wrapsheet material on one side of the absorbent fibrous mass may be bonded to the wrapsheet located on the opposite side of the fibrous mass to effectively entrap the absorbent core 103.

The diaper 101 may also include a ventilation layer (not shown) that is positioned between the absorbent core 103 and the outer cover 117. When utilized, the ventilation layer may help insulate the outer cover 117 from the absorbent core 103, thereby reducing dampness in the outer cover 117. Examples of such ventilation layers may include a nonwoven web laminated to a breathable film, such as described in U.S. Pat. No. 6,663,611 to Blaney, et al., which is incorporated herein in its entirety by reference thereto for all purpose. Such nonwoven webs may be formed in accordance with the present invention.

The diaper 101 may also include a pair of ears (not shown) that extend from the side edges 132 of the diaper 101 into one of the waist regions. The ears may be integrally formed with a selected diaper component. For example, the ears may be integrally formed with the outer cover 117 or from the material employed to provide the top surface. In alternative configurations, the ears may be provided by members connected and assembled to the outer cover 117, the top surface, between the outer cover 117 and top surface, or in various other configurations. As representatively illustrated in FIG. 7, the diaper 101 may also include a pair of containment flaps 112 that are configured to provide a barrier and to contain the lateral flow of body exudates. The containment flaps 112 may be located along the laterally opposed side edges 132 of the bodyside liner 105 adjacent the side edges of the absorbent core 103. The containment flaps 112 may extend longitudinally along the entire length of the absorbent core 103, or may only extend partially along the length of the absorbent core 103. When the containment flaps 112 are shorter in length than the absorbent core 103, they may be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704, 116 to Enloe, which is incorporated herein in its entirety by reference thereto for all purposes.

The diaper 101 may include various elastic or stretchable materials, such as a pair of leg elastic members 106 affixed to the side edges 132 to further prevent leakage of body exudates and to support the absorbent core 103. In addition, a pair of waist elastic members 108 may be affixed to longitudinally opposed waist edges 115 of the diaper 101. The leg elastic members 106 and the waist elastic members 108 are generally adapted to closely fit about the legs and waist of the wearer in use to maintain a positive, contacting relationship with the wearer and to effectively reduce or eliminate the leakage of body exudates from the diaper 101. As used herein, the terms "elastic" and "stretchable" include any material that may be stretched and return to its original shape when relaxed. Suitable polymers for forming such materials include, but are not limited to, block copolymers of polystyrene, polyisoprene and polybutadiene; copolymers of ethylene, natural rubbers and urethanes, etc. Particularly suitable are styrene-butadiene block copolymers sold by Kraton Polymers of Houston, Tex. under the trade name Kraton®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels.

The diaper 101 may also include one or more fasteners 130. For example, two flexible fasteners 130 are illustrated in FIG. 7 on opposite side edges of waist regions to create a waist opening and a pair of leg openings about the wearer. The shape of the fasteners 130 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 130 includes a separate piece of hook material affixed to the inside surface of a flexible backing.

The various regions and/or components of the diaper 101 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 may be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, may also be assembled into the diaper 101 using any attachment mechanism.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. Nos. 5,649,916 to DiPalma, et al.; 6,110,158 to Kielpikowski; 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. Nos. 4,886,512 to Damico et al.; 5,558,659 to Sherrod et al.; 6,888,044 to Fell et al.; and 6,511,465 to Freiburger et al., all of which are incorporated herein in their entirety by reference thereto for all purposes.

The present invention may be better understood with reference to the following examples.

Test Methods

Molecular Weight:

The molecular weight distribution of a polymer was determined by gel permeation chromatography ("GPC"). The samples were initially prepared by adding 0.5% wt/v solutions of the sample polymers in chloroform to 40-milliliter glass vials. For example, 0.05±0.0005 grams of the polymer was added to 10 milliliters of chloroform. The prepared samples were placed on an orbital shaker and agitated overnight. The dissolved sample was filtered through a 0.45-micron PTFE membrane and analyzed using the following conditions:

| | |
|---|---|
| Columns: | Styragel HR 1, 2, 3, 4, & 5E (5 in series) at 41° C. |
| Solvent/Eluent: | Chloroform @ 1.0 milliliter per minute |
| HPLC: | Waters 600 E gradient pump and controller, Waters 717 auto sampler |
| Detector: | Waters 2414 Differential Refractometer at sensitivity = 30, at 40° C. and scale factor of 20 |
| Sample Concentration: | 0.5% of polymer "as is" |
| Injection Volume: | 50 microliters |
| Calibration Standards: | Narrow MW polystyrene, 30-microliter injected volume. |

Number Average Molecular Weight ($MW_n$), Weight Average Molecular Weight ($MW_w$) and first moment of viscosity average molecular weight ($MW_z$) were obtained.

Apparent Viscosity:

The rheological properties of polymer samples were determined using a Gottfert Rheograph 2003 capillary rheometer with WinRHEO version 2.31 analysis software. The setup included a 2000-bar pressure transducer and a 30/1:0/180 roundhole capillary die. Sample loading was done by alternating between sample addition and packing with a ramrod. A 2-minute melt time preceded each test to allow the polymer to completely melt at the test temperature (usually 160 to 220° C.). The capillary rheometer determined the apparent viscosity (Pa·s) at seven different shear rates: 50, 100, 200, 500, 1000, 2000 and 5000 $s^{-1}$. The resultant rheology curve of apparent shear rate versus apparent viscosity gave an indication of how the polymer would run at that temperature in an extrusion process.

Melt Flow Index:

The melt flow index is the weight of a polymer (in grams) forced through an extrusion rheometer orifice (0.0825-inch diameter) when subjected to a force of 2160 grams in 10 minutes at 190° C. The melt flow index was measured in accordance with ASTM Test Method D1238-E.

Thermal Properties: (Melting Point, $T_g$, and % Crystallinity):

The melting temperature, glass transition temperature and degree of crystallinity of a material were determined by differential scanning calorimetry (DSC). The differential scanning calorimeter was a THERMAL ANALYST 2910 Differential Scanning Calorimeter, which was outfitted with a liquid nitrogen cooling accessory and with a THERMAL ANALYST 2200 (version 8.10) analysis software program, both of which are available from T.A. Instruments Inc. of New Castle, Del. To avoid directly handling the samples, tweezers or other tools were used. The samples were placed into an aluminum pan and weighed to an accuracy of 0.01 milligram on an analytical balance. A lid was crimped over the material sample onto the pan. Typically, the resin pellets were placed directly in the weighing pan, and the fibers were cut to accommodate placement on the weighing pan and covering by the lid.

The differential scanning calorimeter was calibrated using an indium metal standard and a baseline correction was performed, as described in the operating manual for the differential scanning calorimeter. A material sample was placed into the test chamber of the differential scanning calorimeter for testing, and an empty pan is used as a reference. All testing was run with a 55-cubic centimeter per minute nitrogen (industrial grade) purge on the test chamber. For resin pellet samples, the heating and cooling program was a 2-cycle test that began with an equilibration of the chamber to −25° C., followed by a first heating period at a heating rate of 10° C. per minute to a temperature of 200° C., followed by equilibration of the sample at 200° C. for 3 minutes, followed by a first cooling period at a cooling rate of 20° C. per minute to a temperature of −25° C., followed by equilibration of the sample at −25° C. for 3 minutes, and then a second heating period at a heating rate of 10° C. per minute to a temperature of 200° C. For fiber samples, the heating and cooling program was a 1-cycle test that began with an equilibration of the chamber to −25° C., followed by a heating period at a heating rate of 20° C. per minute to a temperature of 200° C., followed by equilibration of the sample at 200° C. for 3 minutes, and then a cooling period at a cooling rate of 10° C. per minute to a temperature of −25° C. All testing was run with a 55-cubic centimeter per minute nitrogen (industrial grade) purge on the test chamber.

The results were then evaluated using the THERMAL ANALYST 2200 analysis software program, which identified and quantified the glass transition temperature ($T_g$) of inflection, the endothermic and exothermic peaks, and the areas under the peaks on the DSC plots. The glass transition temperature was identified as the region on the plot-line where a distinct change in slope occurred, and the melting temperature was determined using an automatic inflection calculation. The areas under the peaks on the DSC plots were determined in terms of joules per gram of sample (J/g). For example, the endothermic heat of melting of a resin or fiber sample was determined by integrating the area of the endothermic peak. The area values were determined by converting the areas under the DSC plots (e.g. the area of the endotherm) into the units of joules per gram (J/g) using computer software. The % crystallinity was calculated as follows:

$$\% \text{ crystallinity} = 100 * (A-B)/C$$

wherein,

A is the sum of endothermic peak areas (J/g);

B is the sum of exothermic peak areas (J/g); and

C is the endothermic heat of melting value for the selected polymer where such polymer has 100% crystallinity (J/g). For polylactic acid, C is 93.7 J/g (Cooper-White, J. J., and Mackay, M. E., *Journal of Polymer Science*, Polymer Physics Edition, p. 1806, Vol. 37, (1999)). The areas under any exothermic peaks encountered in the DSC scan due to insufficient crystallinity were subtracted from the area under the endothermic peak to appropriately represent the degree of crystallinity.

Tensile Properties:

The strip tensile strength values were determined in substantial accordance with ASTM Standard D-5034. Specifically, a nonwoven web sample was cut or otherwise provided with size dimensions that measured 25 millimeters (width)× 127 millimeters (length). A constant-rate-of-extension type of tensile tester was employed. The tensile testing system was a MTS SYNERGY 200 Tensile Tester, which is available from MTS Systems Corporation of Eden Prairie, Minn. The tensile tester was equipped with TESTWORKS 4.08B software from MTS Corporation to support the testing. An appropriate load cell was selected so that the tested value fell within the range of 10-90% of the full scale load. The sample was held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run at a 300-millimeter per minute rate with a gauge length of 76 millimeters and a break sensitivity of 40%.

Three samples were tested by applying the test load along the machine-direction and three samples were tested by applying the test load along the cross direction. In addition to tensile strength, the peak load, peak elongation (i.e., % elongation at peak load), and the energy to peak were measured. The peak strip tensile loads from each specimen tested were arithmetically averaged to determine the MD or CD tensile strength.

Cup Crush:

The cup crush test evaluates fabric stiffness by measuring the peak load (also called the "cup crush load" or just "cup crush") required for a 4.5 cm diameter hemispherically shaped foot to crush a 23 cm by 23 cm piece of fabric shaped into an approximately 6.5 cm diameter by 6.5 cm tall inverted cup, while the cup shaped fabric is surrounded by an approximately 6.5 cm diameter cylinder to maintain a uniform deformation of the cup shaped fabric. An average of 10 readings is used. The foot and the cup are aligned to avoid contact between the cup walls and the foot that could affect the peak load. The peak load is measured while the foot is descending at a rate of about 0.25 inches per second (38 cm per minute) and is measured in grams. The cup crush test also yields a value for the total energy required to crush a sample ("the cup crush energy"), which is the energy from the start of the test to the peak load point, i.e. the area under the curve formed by the load in grams on one axis and the distance the foot travels in millimeters on the other. Lower cup crush values indicate a softer web. A suitable device for measuring cup crush is a model FTD-G-500 load cell (500 gram range) available from the Schaevitz Company, Pennsauken, N.J. The cup crush values are reported as grams-force.

Trapezoid Tear

The trapezoid or "trap" tear test is a tension test applicable to the nonwoven web. The entire width of the specimen is gripped between clamps, thus the test primarily measures the bonding or interlocking and strength of individual fibers directly in the tensile load, rather than the strength of the composite structure of the fabric as a whole. The test measures the fabric resistance to tear propagation under a constant rate of extension. A fabric cut on one edge is clamped along nonparallel sides of a trapezoidal shaped specimen and is pulled, causing a tear propagation in the specimen perpendicular to the load. The test can be conducted in either the MD or CD direction. In conducting the trap tear test, an outline of a trapezoid is drawn on a 3 by 6 inch (75 by 152 mm) specimen with the longer dimension in the direction being tested, and the specimen is cut in the shape of the trapezoid. The trapezoid has a 4 inch (102 mm) side and a 1 inch (25 mm) side which are parallel and which are separated by 3 inches (76 mm). A small preliminary cut of ⅝ inches (15 mm) is made in the middle of the shorter of the parallel sides. The specimen is clamped in, for example, an Instron Model™ (a constant-rate-of-extension tester), available from the Instron Corporation, 2500 Washington St., Canton, Mass., or a Thwing-Albert Model INTELLECT II available from the Thwing-Albert Instrument Co., 10960 Dutton Rd., Phila., Pa. 19154, which have 3 inch (76 mm) long parallel clamps. The specimen is clamped along the non-parallel sides of the trapezoid so that the fabric on the longer side is loose and the fabric along the shorter side taut, and with the cut halfway between the clamps. A continuous load is applied on the specimen such that the tear propagates across the specimen width. It should be noted that the longer direction is the direction being tested even though the tear is perpendicular to the length of the specimen. The force required to completely tear the specimen is recorded in pounds with higher numbers indicating a greater resistance to tearing. The test method used conforms to ASTM Standard test D1117-14, except that the tearing load is calculated as the average of the first and highest peaks recorded rather than the lowest and highest peaks. Five specimens for each sample are typically tested. The data presented include first and high peak values.

Lister Intake:

The Lister test is used to determine the liquid strike-through time of a test sample of nonwoven fabric. The strike-through time is the time taken by a specified amount of liquid to be absorbed in the nonwoven fabric. One suitable test procedure is the EDANA test No. 150.9-1 (liquid strike-through time test). According to one method, a 4 inch by 4 inch (10.2 cm×10.2 cm) sample of the selected nonwoven fabric material is weighed and placed on a 4 inch by 4 inch (10.2 cm×10.2 cm) assembly of 5-ply filter paper, type ERT FF3 (available from: Hollingsworth and Vose Co., East Walpole, Mass.). The sample assembly is then placed under a Lister tester. A suitable Lister tester is available from W. Fritz Mezger Inc., Spartanburg, S.C. A strike-through plate is employed for the testing, and is positioned over the test sample and under the Lister test equipment. A 5 mL amount of 0.9% saline is delivered onto the sample assembly. The time to absorb the liquid (strike-through time) is measured automatically by the Lister testing equipment and displayed. Subsequently, a new 5-ply blotter assembly is quickly placed underneath the nonwoven sample within 20 seconds, and the 5 mL delivery of saline is repeated. In total, the 5 mL delivery of liquid is performed 5 times on the selected nonwoven sample, and each strike-through time is recorded. The sample is weighed again after the sequence of 5 tests. For a given nonwoven fabric sample, the 5-sequence test is repeated three times, and the 15 results are averaged to provide the strike-through time of the material.

Abrasion Resistance:

The "reciprocating abrasion test" (RAT) involves stroking a sample, usually 5.5 inch×7 inch (140 mm×180 mm) of fabric with a silicone rubber abrasive and then evaluating the fabric for pilling, roping and fuzzing. A horizontally reciprocating dual head abrasion tester was obtained from United States Testing Company, Inc. of Hoboken N.J. (Model No. 8675). The abradant, silicone solid rubber fiber glass reinforced material had a Shore A rubber surface hardness of 81±9 and had a size of 36 inches (914 mm)×4 inches (102 mm)×0.005 inches (0.127 mm) (available as Catalogue No. 4050 from Flight Insulations Inc.). Prior to testing, the sample and equipment were conditioned to standard temperature and humidity by cycling about 200 times over a scrap piece of the material to be tested. The test sample was generally free of folds and creases, and mounted in the instrument on cork backing and cleaned of residual surface fibers with a brush. The abradant arm was lowered and the cycling begun at a total weight of 2.6 pounds (1180 grams) with one half of the weight on each of the two abradant arms. After a set number of cycles, each sample was removed from the machine and compared to a standard set of photographs. Each sample was assigned a number based on a comparison of the abraded material to the standard photograph. Five (5) is the best rating with one (1) being the worst rating.

EXAMPLE 1

Various physical properties of the following aliphatic polyesters were tested.

P1: Polybutylene succinate obtained from IRE Chemicals, South Korea under the name EnPol™ G4500 (Grade CE272);

P2: Polybutylene succinate obtained from IRE Chemicals, South Korea under the name EnPol™ G4500 (Grade 1 DF241);

P3: Polybutylene succinate obtained from IRE Chemicals, South Korea under the name EnPol™ G4500 (Grade 2DF242);

P4: Polybutylene succinate obtained from IRE Chemicals, South Korea under the name EnPol™ G4560J;

P5: Polybutylene succinate obtained from IRE Chemicals, South Korea under the name EnPol™ G4500 (Grade CE272-High MFI);

P6: Polybutylene succinate obtained from IRE Chemicals, South Korea under the name EnPol™ G4500 (Grade CE272-Mid MFI);

P7: Polybutylene succinate obtained from Showa, Japan under the name Bionolle™ 1020;

P8: Polybutylene succinate obtained from Showa, Japan under the name Bionolle™ 1903;

P9: Polybutylene succinate obtained from Showa, Japan under the name Bionolle™ 1003;

P10: Polylactic acid obtained from Biomer Inc., Germany under the name Biomer™ L9000;

P11: Polylactic acid obtained from Natureworks, LLC under the name EcoPla™ 6201 D; and P12: Polylactic acid obtained from Natureworks, LLC under the name EcoPla™ 6300.

The results are set forth below in Tables 1 and 2.

As indicated, the Bionolle™ polymers (P7-P9) were quite viscous compared to the EnPol™ G4500 polymers (P2-P4).

EXAMPLE 2

The ability to form a nonwoven web in accordance with the present invention was demonstrated. As indicated in Table 3 below, various combinations of polymers were tested. The polylactic acid and polybutylene succinate polymers were placed in separate desiccant driers and dried at temperature and time conditions within supplier recommendations. Each polymer was then pneumatically conveyed with dry air to separate extruder hoppers, which were also sealed to prevent moisture pickup. The polylactic acid polymer was fed into extruder A, and the polybutylene succinate polymer was fed into extruder B. The heating profile of Extruder A was set to achieve a final polylactic acid polymer melt at a temperature of 215° C. to 230° C. at a throughput of 210 to 270 kilograms per hour. The heating profile of Extruder B was set to achieve a final polybutylene succinate polymer melt at a temperature of 200° C. to 215° C. at a throughput of 30 to 90 kilograms per hour. Each extruder pumped their respective melt streams through a melt filter of standard mesh size and to a metering pump. Each of the positive displacement pumps controlled the throughput of the polymers at the aforementioned throughputs. The extruder rpm range was set to control to a constant pump inlet pressure standard to persons skilled in the art. The molten polymers were then separately fed into a single heated spin pack assembly. The spin pack assembly arranged to two polymer streams in to an array of filaments exiting the spinneret in a sheath-core bicomponent configuration. The sheath was comprised of polybutylene succinate polymer and the core was comprised of polylactic acid poly-

TABLE 1

Molecular Weight and Melt Properties

| Polymer | $MW_n$ | $MW_w$ | Polydispersity Index | Melt Flow Index (190° C., 2.16 kg) | Melt Temp (° C.) | Heat of Fusion, (J/g) | Crystallization Temp. (° C.) | Heat of Crystallization (J/g) |
|---|---|---|---|---|---|---|---|---|
| P1 | 78,000 | 126,900 | 1.63 | 47 | 114.95 | 49.45 | 79.08 | 57.86 |
| P2 | 59,500 | 99,200 | 1.67 | 150 | 114.94 | 64.26 | 70.86 | 62.38 |
| P3 | 72,300 | 122,900 | 1.70 | 41 | 115.03 | 59.69 | 75.13 | 61.26 |
| P4 | 77,600 | 142,900 | 1.84 | 25 | 114.40 | — | — | — |
| P5 | 49,900 | 92,400 | 1.85 | 127 | 113.21 | 71.48 | 64.90 | 72.34 |
| P6 | 61,500 | 105,400 | 1.71 | 56 | 114.06 | 58.54 | 68.02 | 61.25 |
| P7 | — | — | — | 28 | 114.28 | 56.88 | 76.36 | 64.13 |
| P8 | — | — | — | — | — | — | — | — |
| P9 | — | — | — | 4.4 | — | — | — | — |
| P10 | 113.5 | 150.7 | 1.33 | 22 (210° C.) 43 (230° C.) | 169.60 | 3.70 | 71.38 | 33.46 |

TABLE 2

Rheological Properties (30/1/180 Roundhole)

| Apparent Shear Rate | Apparent Viscosity (Pa-s) (at 160° C.) | | | | | | Apparent Viscosity (Pa-s) (at 220° C.) | | |
|---|---|---|---|---|---|---|---|---|---|
| (sec$^{-1}$) | P4 | P2 | P3 | P7 | P8 | P9 | P4 | P10 | P3 |
| 50 | 407.1 | — | — | — | — | — | 65.1 | — | 98.0 |
| 100 | 325.7 | — | — | — | — | — | 48.9 | — | 73.3 |
| 200 | 268.7 | 86.0 | 212 | 395 | 578 | 973 | 44.8 | — | 73.3 |
| 500 | 192.2 | 76.0 | 163 | 293 | 360 | 621 | 44.0 | 261.0 | 63.5 |
| 1000 | 141.7 | 66.0 | 129 | 217 | 241 | 416 | 39.0 | 195.4 | 44.8 |
| 2000 | — | 53.3 | 95.3 | 148 | 157 | 248 | — | 179.0 | — |
| 5000 | — | 37.0 | 57 | 80.8 | 86.8 | — | — | 168.0 | — | mer. The total pump rate was 300 kilograms per hour. Individual pump rates were adjusted at different moments to produce filaments in the range of 10% to 90% sheath and 30% to 70% core. The bicomponent filaments exiting the spinneret were quenched at standard air flows and air temperatures according to persons skilled in the art using a spunbond line available from Reifenhäuser GmbH & Co. KG Maschinenfabrik under the designation REICOFIL® 4. The filaments were pneumatically drawn down to a final diameter of between 14 to 16 micrometers.

The filaments were then deposited directly onto a foraminous surface under vacuum to make a randomly formed nonwoven web. The foraminous surface rotated to form a nonwoven web at 300 kilograms per hour. Directly after the filaments formed a web, the web was annealed and stabilized under a rotating roll with a surface temperature 40° C. to 60° C. and a standard nip pressure in a manner familiar to persons skilled in the art. The stabilized web was then transferred through a calender roll nip and subjected to heat and pressure. The bond pattern was a diamond bond pattern of less than 30% bond area and greater than 100 pins per square inch. The bonded web was then wound on a surface driven winder of standard design to persons skilled in the art. The web forming conditions for the samples are set forth below in Table 3 in more detail.

TABLE 3

Web Forming Conditions

| Sample | Sheath | Core | Chamber Draw Pressure (kPA) | Chamber Air Temps (° C.) | GHM | Bond Roll Temps (° C.) | Bond Roll Pressure (psi) | Line Speed (m/min) | Fiber Size (μm) | Basis Wt. (g/m²) |
|---|---|---|---|---|---|---|---|---|---|---|
| 1 | — | P11 | 10 | 51/70 | 0.83 | NA | 39 | 20 | 13 | 61 |
| 2 | — | P11 | 10 | 51/70 | 0.83 | NA | 39 | 101 | 13 | 62 |
| 3 | — | P11 | 10 | 50/70 | 0.83 | 160/155 | 80 | 170 | 13 | 38 |
| 4 | — | P11 | 10 | 50/70 | 0.83 | 155/150 | 80 | 170 | 13 | 39 |
| 5 | — | P11 | 9.5 | 50/70 | 0.67 | 147/137 | 68 | 165 | 11.9 | 27.4 |
| 6 | — | P11 | 9.5 | 51/70 | 0.67 | 147/137 | 68 | 173 | — | 26.8 |
| 7 | — | P12 (10%) P11 (90%) | 9.3 | 51/70 | 0.67 | 145/137 | 108 | 173 | — | 25.7 |
| 8 | — | P12 (20%) P11 (80%) | 9.21 | 51/70 | 0.67 | 145/137 | 108 | 173 | — | 27.4 |
| 9 | — | P12 (20%) P11 (80%) | 9.5 | 50/70 | 0.67 | 148/140 | 108 | 173 | — | 27.1 |
| 10 | — | P12 (20%) P11 (80%) | 9.5 | 50/70 | 0.67 | 151/143 | 108 | 173 | — | 27.1 |
| 11 | P4 (20%) | P11 (80%) | 3 | 30/30 | 0.67 | 110/105 | 58 | 180 | 17.4 | 25.4 |
| 12 | P4 (30%) | P11 (70%) | 3 | 30/30 | 0.67 | 110/105 | 58 | 180 | 17 | 25.4 |
| 13 | P4 (10%) | P11 (90%) | 3 | 30/30 | 0.67 | 110/105 | 58 | 180 | 16.2 | 26.4 |
| 14 | P4 (20%) | P11 (80%) | 5 | 40/40 | 0.67 | 110/105 | 58 | 180 | 16.2 | 18.9 |
| 15 | — | P4 | 3 | 15/15 | 0.67 | 100/95 | 20 | 180 | — | 21.1 |

Various properties of the resulting nonwoven webs were tested. The results are set forth below in Tables 4-6.

TABLE 4

Mechanical Properties

| Sample | Peak MD Load (g/2 inch) | Std. Dev. | % Elongation at MD Peak Load | Peak CD Load (g/2 inch) | Std. Dev. | % Elongation at CD Peak Load | MD Toughness (in * $lb_f$) | Std. Dev. | CD Toughness (in * $lb_f$) | Std. Dev. |
|---|---|---|---|---|---|---|---|---|---|---|
| 1 | 4027 | 305 | 4.16 | 714 | 50 | 34.8 | 0.7 | 0.2 | 1.31 | 0.8 |
| 2 | 3759 | 386 | 3.95 | 572 | 45 | 57 | 0.53 | 0.1 | 1.77 | 0.7 |
| 3 | 4559 | 145 | 4.7 | 827 | 45 | 16.3 | 0.92 | 0.1 | 0.58 | 0.1 |
| 4 | 4214 | 168 | 3.66 | 936 | 122 | 15.7 | 0.63 | 0.1 | 0.66 | 0.2 |
| 5 | 2007 | 169 | 4 | 545 | 47 | 20.2 | 0.32 | 0 | 0.486 | 0 |
| 6 | 2490 | 129 | 4 | 789 | 104 | 16.3 | 0.43 | 0 | 0.499 | 0.2 |
| 7 | 2330 | 173 | 3.3 | 637 | 124 | 15.1 | 0.33 | 0.1 | 0.398 | 0.2 |
| 8 | 3216 | 164 | 4.8 | 1031 | 166 | 20.7 | 0.666 | 0.1 | 0.849 | 0.2 |
| 9 | 3265 | 198 | 5.1 | 1071 | 105 | 18.2 | 0.698 | 0.1 | 0.799 | 0.2 |
| 10 | 3255 | 111 | 5.4 | 1043 | 158 | 21.5 | 0.779 | 0.2 | 0.828 | 0.2 |
| 11 | 4545 | 167 | 48.9 | 2745 | 166 | 56 | 10.01 | 1.1 | 6.34 | 0.8 |
| 12 | 4756 | 264 | 47.2 | 3120 | 168 | 56 | 10.05 | 1.1 | 6.85 | 0.7 |
| 13 | 2905 | 341 | 26.1 | 1730 | 120 | 35.3 | 3.75 | 1 | 2.68 | 0.4 |
| 14 | 4319 | 854 | 33.6 | 1792 | 99 | 52.6 | 6.62 | 2 | 3.7 | 0.5 |
| 15 | 1896 | 145 | 36.1 | 1273 | 85 | 52.4 | 2.93 | 0.6 | 2.42 | 0.3 |

| Sample | CD Toughness/ MD Toughness | MD Peak Load/ Basis Wt. | Specific MD Toughness | Specific CD Toughness | Observation |
|---|---|---|---|---|---|
| 1 | 0.18 | 66 | 0.31 | 0.58 | soft, no molten mass in bonds |
| 2 | 0.15 | 61 | 0.23 | 0.77 | soft, no molten mass in bonds |
| 3 | 0.18 | 120 | 0.65 | 0.41 | soft, molten mass in bond points |

TABLE 4-continued

Mechanical Properties

| | | | | | |
|---|---|---|---|---|---|
| 4 | 0.22 | 108 | 0.44 | 0.46 | soft, molten mass in bond points, somewhat less melting |
| 5 | 0.27 | 73 | 0.32 | 0.48 | soft, no molten mass in bonds |
| 6 | 0.32 | 93 | 0.43 | 0.50 | soft, no molten mass in bonds |
| 7 | 0.27 | 91 | 0.35 | 0.42 | soft |
| 8 | 0.32 | 117 | 0.66 | 0.84 | soft |
| 9 | 0.33 | 120 | 0.70 | 0.80 | soft, molten mass in bond points |
| 10 | 0.32 | 120 | 0.78 | 0.82 | soft, molten mass in bond points, somewhat less melting |
| 11 | 0.60 | 179 | 10.64 | 6.74 | soft, strong |
| 12 | 0.66 | 187 | 10.68 | 7.28 | soft, strong |
| 13 | 0.60 | 110 | 3.84 | 2.74 | somewhat rough |
| 14 | 0.41 | 229 | 9.46 | 5.29 | soft, strong, low basis weight |
| 15 | 0.67 | 90 | 3.75 | 3.10 | very soft sample, weak |

TABLE 5

Abrasion Resistance and Water Absorption

| Sample | Basis Weight | | RAT Fuzzing MD Anvil (in) | RAT Roping MD Anvil (in) | RAT Rating MD Anvil (rating) | Lister 1st Insult Face (sec) |
|---|---|---|---|---|---|---|
| Control | 18 | | 0.48 | 1.80 | 4.00 | 213.964 |
| | | Std. Dev. | 0.20 | 1.10 | 0.70 | 122.2 |
| 5 | 26.5 | | 0.86 | 2.38 | 3.60 | 71.894 |
| | | Std. Dev. | 0.20 | 1.06 | 0.89 | 127.54 |
| 7 | 25.7 | | 0.72 | 1.68 | 4.60 | 300 |
| | | Std. Dev. | 0.11 | 2.37 | 0.55 | 0.00 |
| 8 | 27.4 | | 0.56 | 0.52 | 4.80 | 300 |
| | | Std. Dev. | 0.13 | 1.11 | 0.45 | 0.00 |
| 9 | 27.1 | | 0.52 | 0.38 | 5.00 | 244 |
| | | Std. Dev. | 0.11 | 0.41 | 0 | 124.80 |
| 11 | 25.4 | | 1.08 | 0.22 | 4.60 | 19.3 |
| | | Std. Dev. | 0.58 | 0.27 | 0.55 | 9.26 |
| 12 | 25.4 | | 1.20 | 0.04 | 4.80 | 85.1 |
| | | Std. Dev. | 0.57 | 0.06 | 0.45 | 88.87 |
| 13 | 26.4 | | 1.20 | 0.18 | 4.40 | 7.0 |
| | | Std. Dev. | 0.26 | 0.11 | 0.55 | 2.37 |
| 14 | 19 | | 1.02 | 0.10 | 4.80 | 19.0 |
| | | Std. Dev. | 0.60 | 0.10 | 0.45 | 17.59 |
| 15 | 21.1 | | 0.34 | 0 | 5.00 | 5.0 |
| | | Std. Dev. | 0.22 | 0 | 0 | 1.05 |

| Sample | Lister 2nd Insult Face (sec) | Lister 3rd Insult Face (sec) | Lister 4th Insult Face (sec) | Lister 5th Insult Face (sec) | Lister Spec. Wgt. Diff Face (g) | Average Lister Average of Five Face (sec) |
|---|---|---|---|---|---|---|
| Control | 216.46 | 114.496 | 78.186 | 97.294 | 0.065 | 144 |
| | 125.6 | 113.7 | 124.4 | 118.5 | 0.0 | — |
| 5 | 55.31 | 41.736 | 17.114 | 27.006 | 0.042 | 43 |
| | 64.36 | 62.75 | 13.68 | 20.70 | 0.025 | — |
| 7 | 203 | 98 | 71 | 32 | 0.069 | 141 |
| | 136.51 | 118.13 | 77.73 | 24.98 | 0.079 | — |
| 8 | 210 | 137 | 76 | 89 | 0.062 | 162 |
| | 128.41 | 148.53 | 61.01 | 118.85 | 0.075 | — |
| 9 | 185 | 73 | 95 | 102 | 0.171 | 140 |
| | 124.89 | 65.83 | 52.87 | 71.32 | 0.090 | — |
| 11 | 4.6 | 7.4 | 4.9 | 6.7 | 0.001 | 8.6 |
| | 0.73 | 1.72 | 1.26 | 1.71 | 0.004 | — |
| 12 | 5.3 | 4.9 | 5.6 | 4.7 | 0.015 | 21.1 |
| | 2.03 | 1.42 | 2.87 | 1.57 | 0.018 | — |
| 13 | 5.0 | 4.6 | 4.2 | 4.0 | 0.001 | 5.0 |
| | 0.72 | 0.92 | 0.38 | 0.17 | 0.007 | — |
| 14 | 6.7 | 5.1 | 4.9 | 4.8 | 0.007 | 8.1 |
| | 2.20 | 0.86 | 0.43 | 0.49 | 0.006 | — |
| 15 | 4.6 | 5.1 | 5.0 | 6.0 | 0 | 5.1 |
| | 0.29 | 0.90 | 0.73 | 1.11 | 0.001 | — |

TABLE 6

Stiffness and Tear Resistance

| Sample | Basis Weight | | Cup Crush Peak Energy (g_f) | CD Tear Resistance (cN) | MD Tear Resistance (cN) |
|---|---|---|---|---|---|
| Control | 18 | | 42.59 | 236.41 | 341.1 |
| | | Std. Dev. | 5.54 | 28.9 | 52.9 |
| 5 | 26.5 | | 46.05 | 142.59 | 111.31 |
| | | Std. Dev. | 6.62 | 22.0 | 18.9 |
| 7 | 25.7 | | 64.66 | 98.5 | 150.8 |
| | | Std. Dev. | 6.81 | 13.2 | 22.3 |
| 8 | 27.4 | | 79.73 | 137.2 | 209.6 |
| | | Std. Dev. | 11.99 | 43.3 | 38.8 |
| 9 | 27.1 | | 75.09 | 135.4 | 179.8 |
| | | Std. Dev. | 10.89 | 28.6 | 19.1 |
| 11 | 25.4 | | 49.14 | 304.1 | 419.6 |
| | | Std. Dev. | 5.71 | 28.0 | 13.7 |
| 12 | 25.4 | | 45.08 | 240.9 | 349.7 |
| | | Std. Dev. | 6.3 | 13.4 | 40.8 |
| 13 | 26.4 | | 47.73 | 473 | 688.47 |
| | | Std. Dev. | 4.24 | 18.5 | 105.0 |
| 14 | 19 | | 52.08 | 300 | 403.7 |
| | | Std. Dev. | 16.73 | 53.7 | 66.6 |
| 15 | 21.1 | | 7.29 | 143.5 | 217.2 |
| | | Std. Dev. | 0.8 | 23.9 | 23.6 |

As indicated above, the samples formed according to the present invention (i.e., Samples 11-14) exhibited excellent mechanical properties, softness, abrasion resistance, and water absorption characteristics.

Figure 2:
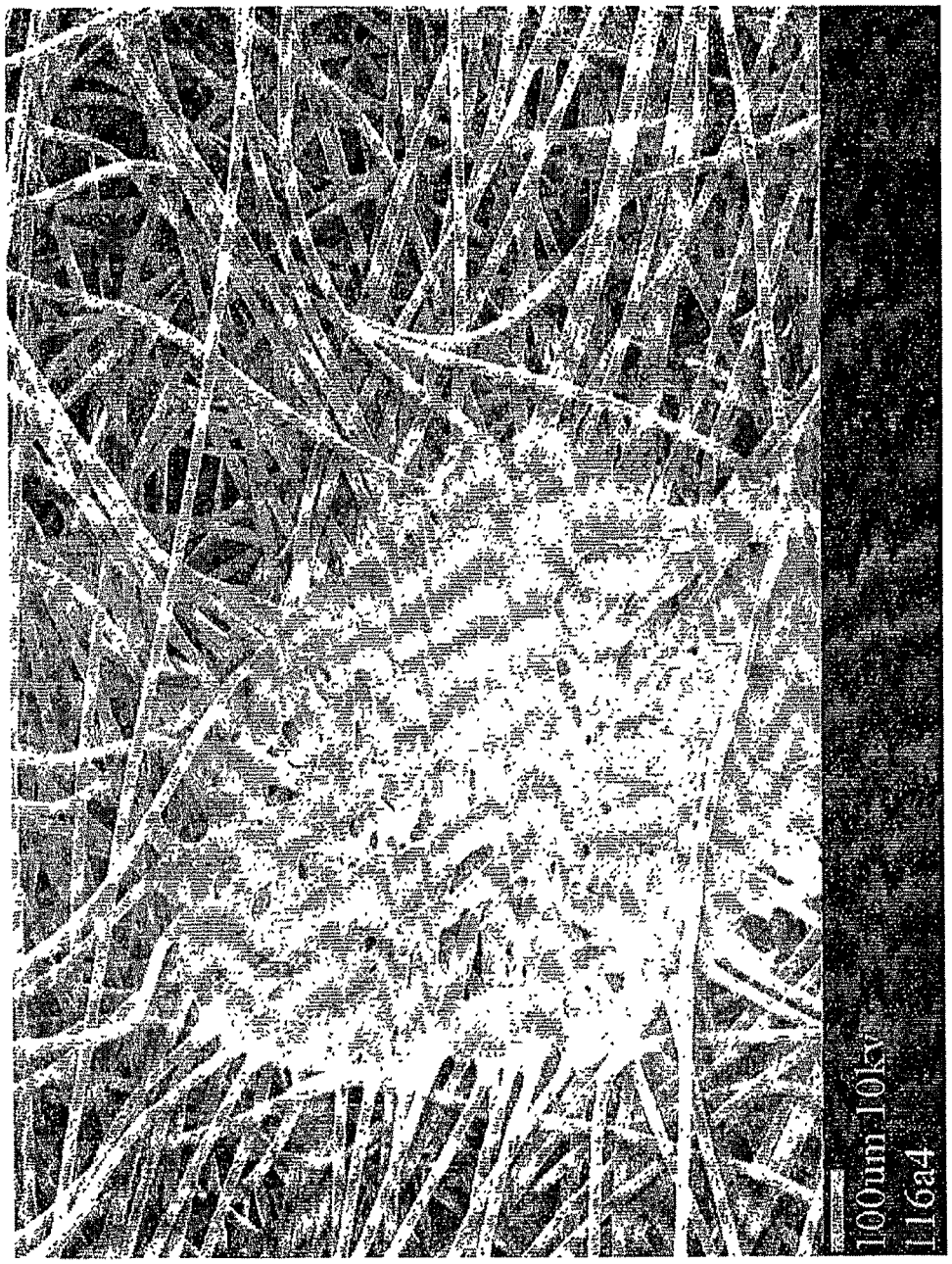
FIG. 2 shows an SEM microphotograph (40×) of Sample No. 3 formed in Example 2.
Figure 3:
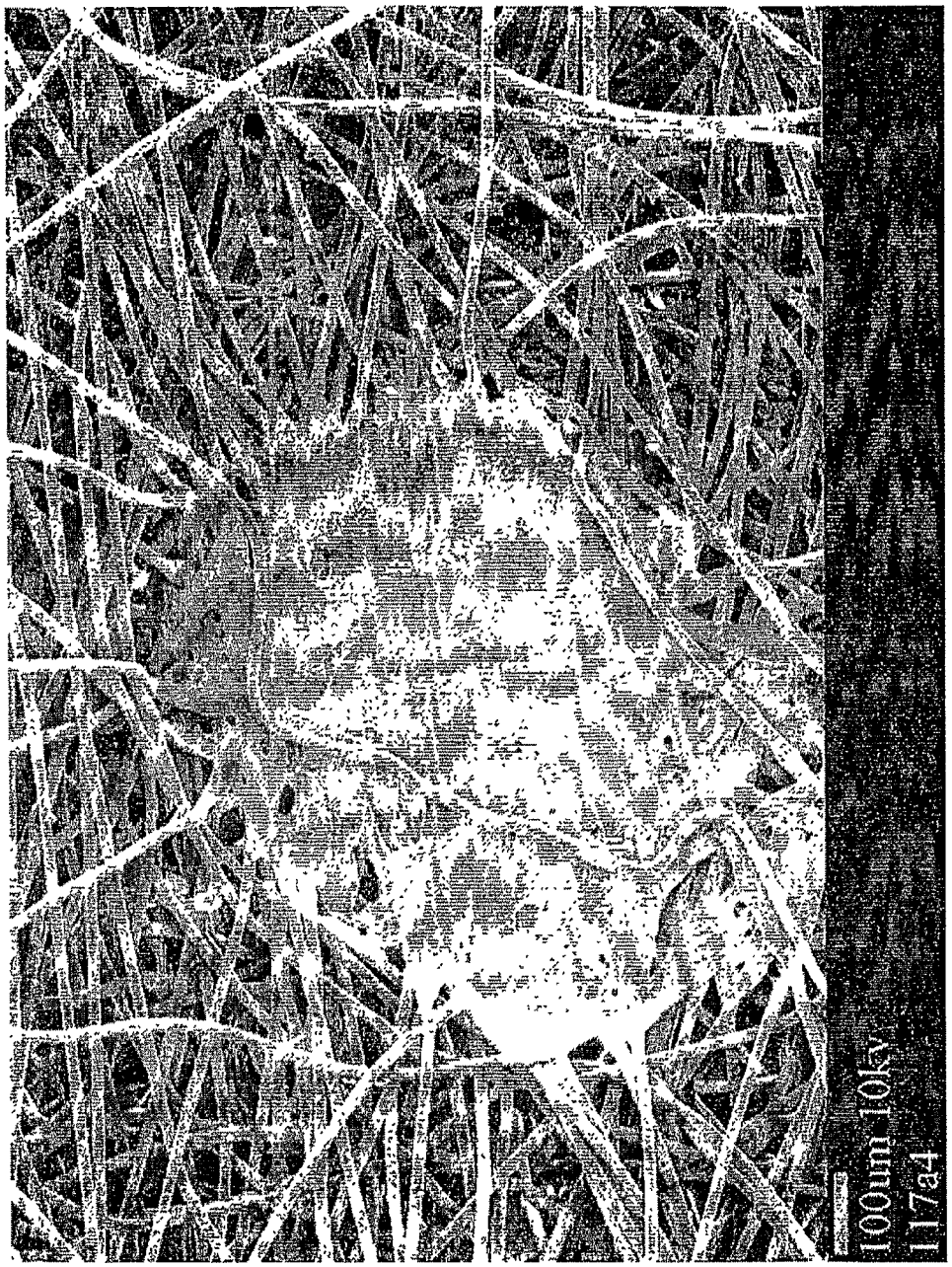
FIG. 3 shows an SEM microphotograph (40×) of Sample No. 4 formed in Example 2.
Figure 4:
FIG. 4 shows an SEM microphotograph (40×) of Sample No. 13 formed in Example 2.
Figure 5:
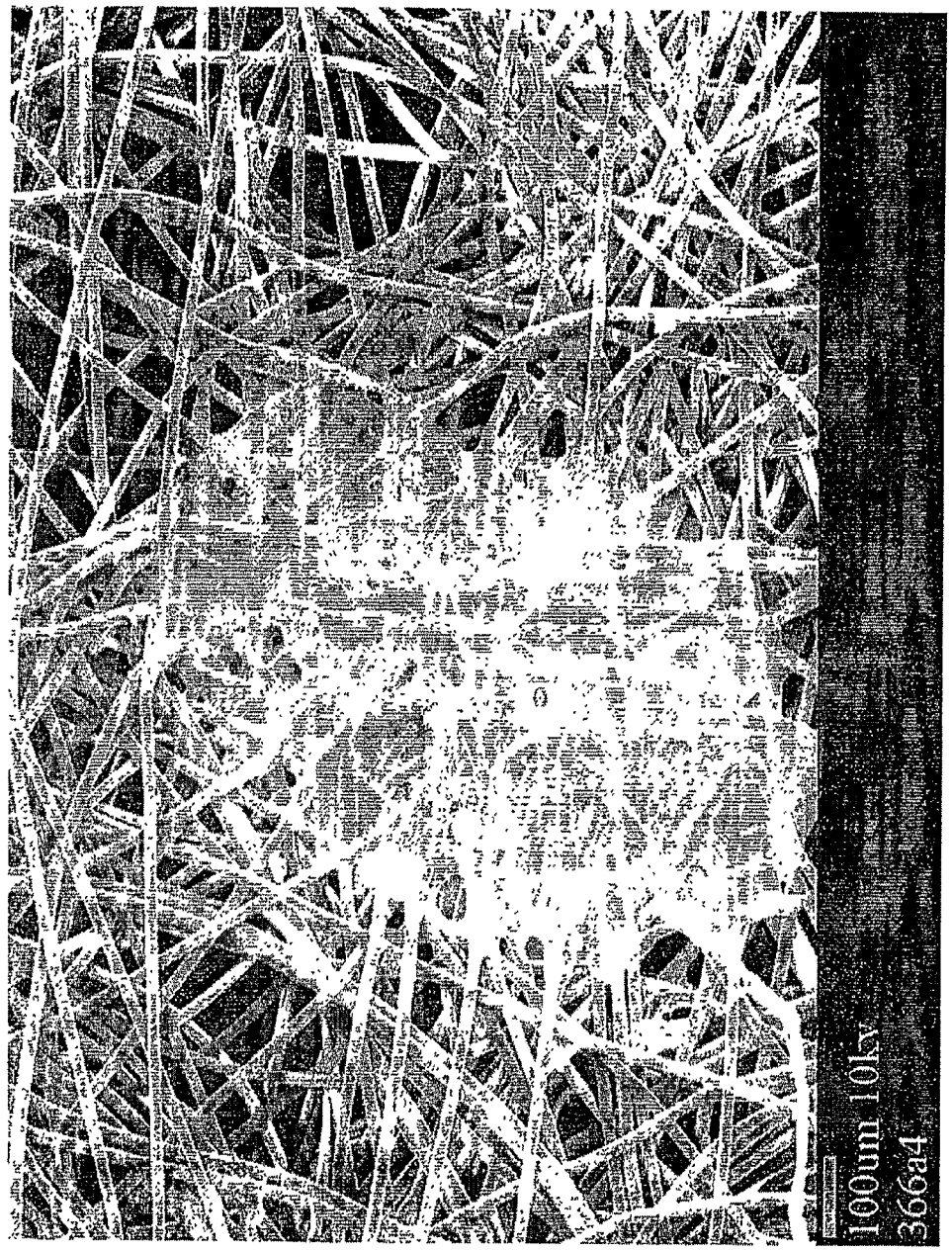
FIG. 5 shows an SEM microphotograph (40×) of Sample No. 11 formed in Example 2.
Figure 6:
FIG. 6 shows an SEM microphotograph (40×) of Sample No. 12 formed in Example 2.

In addition to the tests referenced above, optical micrographs (viewed in transmitted/reflected light) were also taken of the bond points of several samples. For instance, FIGS. 2-3 show bond points for Sample Nos. 3-4, respectively, both of which were formed from 100% polylactic acid. As illustrated, the bond points are poorly defined. Fibers in the bond points are melted and flattened, and the bond point boundary is abrupt lacking smoothness and continuity. On the other hand, FIGS. 4-6 show bond points for Sample 13 (10% PBS sheath), Sample 11 (20% PBS sheath), and Sample 12 (30% PBS sheath), respectively. These samples generally had an increased level of fiber frames within the bond point, and also had a smoother interface at the bond point boundary. In FIG. 5, for instance, fiber frames are clearly visible within the melted polymer puddle. In addition, fiber orientation in the bond point was at least two nearly perpendicular directions, which was also confirmed by Azimuthal X-ray diffraction scans.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A biodegradable nonwoven web comprising substantially continuous multicomponent filaments, wherein the multicomponent filaments comprise a first component and a second component, the first component containing a first aliphatic polyester having a melting point of from about 160° C. to about 250° C. and the second component containing a second aliphatic polyester, wherein the melting point of the second aliphatic polyester is at least about 30° C. less than the melting point of the first aliphatic polyester, and wherein the second aliphatic polyester has a number average molecular weight of from about 30,000 to about 120,000 Daltons, a glass transition temperature of less than about 25° C., and an apparent viscosity of from about 50 to about 215 Pascal-seconds, as determined at a temperature of 160° C. and a shear rate of 1000 sec$^{-1}$, wherein the second component is free of a multi-carboxylic acid nucleating agent.

2. The biodegradable nonwoven web of claim 1, wherein the first aliphatic polyester is polylactic acid.

3. The biodegradable nonwoven web of claim 1, wherein the second aliphatic polyester has an apparent viscosity of from about 80 to about 150 Pascal-seconds, as determined at a temperature of 160° C. and a shear rate of 1000 sec$^{-1}$.

4. The biodegradable nonwoven web of claim 1, wherein the second aliphatic polyester has a melting point at least about 40° C. less than the melting point of the first aliphatic polyester.

5. The biodegradable nonwoven web of claim 1, wherein the second aliphatic polyester has a melting point of from about 100° C. to about 140° C.

6. The biodegradable nonwoven web of claim 1, wherein the second aliphatic polyester has a number average molecular weight of from about 40,000 to about 100,000 Daltons.

7. The biodegradable nonwoven web of claim 1, wherein the second aliphatic polyester has a polydispersity index of from about 1.0 to about 3.0.

8. The biodegradable nonwoven web of claim 1, wherein the second aliphatic polyester has a melt flow index of from about 20 to about 120 grams per 10 minutes, measured at a force of 2160 grams and temperature of 190° C. in accordance with ASTM Test Method D1238-E.

9. The biodegradable nonwoven web of claim 1, wherein the second aliphatic polyester has a glass transition temperature of about 0° C. or less.

10. The biodegradable nonwoven web of claim 1, wherein the second aliphatic polyester has a glass transition temperature of about −10° C. or less.

11. The biodegradable nonwoven web of claim 1, wherein the second aliphatic polyester is polybutylene succinate.

12. The biodegradable nonwoven web of claim 1, wherein the filaments have a sheath/core or side-by-side configuration.

13. The biodegradable nonwoven web of claim 1, wherein the web exhibits a peak elongation in the machine direction of at least about 10%.

14. The biodegradable nonwoven web of claim 1, wherein the web exhibits a peak elongation in the machine direction of at least about 35%.

15. The biodegradable nonwoven web of claim 1, wherein the web exhibits a peak elongation in the cross machine direction of at least about 35%.

16. The biodegradable nonwoven web of claim 1, wherein the web exhibits a peak elongation in the cross machine direction of at least about 50%.

17. The biodegradable nonwoven web of claim 1, wherein the web exhibits a peak load in the machine direction of at least about 3500 grams-force per inch.

18. The biodegradable nonwoven web of claim 1, wherein the web exhibits a peak elongation in the cross machine direction of at least about 1500 grams-force per inch.

19. The biodegradable nonwoven web of claim 1, wherein the filaments are autogenously bonded at intermittent compacted areas.

20. The biodegradable nonwoven web of claim 19, wherein at least a portion of the high melting point aliphatic polyester within the compacted areas retains a substantially fibrous form.

21. The biodegradable nonwoven web of claim 20, wherein the substantially fibrous high melting point polymer is oriented in two or more directions.

22. A method for forming the biodegradable nonwoven web of claim 1, the method comprising:

co-extruding a first thermoplastic composition and a second thermoplastic composition to form the multicomponent filaments, the first thermoplastic composition comprising the first aliphatic polyester and the second thermoplastic composition comprising the second aliphatic polyester;

randomly depositing the filaments onto a forming surface; and melt-fusing the filaments at intermittent bond regions.

23. The method of claim 22, wherein the second thermoplastic composition is extruded at a temperature ranging from about 145° C. to about 195° C.

24. The method of claim 22, wherein the filaments are melt-fused by passing the web through a nip formed between two rolls.

25. The method of claim 24, wherein one or both of the rolls are heated to a temperature of from about 50° C. to about 160° C.

26. The method of claim 24, wherein one or both of the rolls are heated to a temperature of from about 100° C. to about 140° C.

27. The method of claim 24, wherein a pressure of from about 5 to about 150 pounds per square inch is applied at the nip.

28. The method of claim 24, wherein a pressure of from about 30 to about 60 pounds per square inch is applied at the nip.

29. The method of claim 22, wherein the bond regions cover less than 50% of a surface of the web.

30. An absorbent article comprising an absorbent core positioned between a substantially liquid-impermeable layer and a liquid-permeable layer, wherein the substantially liquid-impermeable layer contains the biodegradable nonwoven web of claim 1.

31. The absorbent article of claim 30, wherein the substantially liquid-impermeable layer forms an outer cover of the absorbent article.

32. The absorbent article of claim 30, wherein the biodegradable nonwoven web is laminated to a breathable film.

33. The biodegradable nonwoven web of claim 1, wherein the second aliphatic polyester has a number average molecular weight of from about 45,000 to about 85,000 Daltons.

* * * * *